United States Patent
Sukuru

(10) Patent No.: US 12,303,557 B2
(45) Date of Patent: May 20, 2025

(54) COLLAGENASE FORMULATIONS AND METHODS OF PRODUCING THE SAME

(71) Applicant: ENDO OPERATIONS LIMITED, Dublin (IE)

(72) Inventor: Karunakar Sukuru, Garnet Valley, PA (US)

(73) Assignee: Endo Operations Limited, Dublin (IE)

( * ) Notice: Subject to any disclaimer, the term of this patent is extended or adjusted under 35 U.S.C. 154(b) by 0 days.

(21) Appl. No.: 18/478,368

(22) Filed: Sep. 29, 2023

(65) Prior Publication Data

US 2024/0041993 A1 Feb. 8, 2024

Related U.S. Application Data

(63) Continuation of application No. 17/419,899, filed as application No. PCT/US2020/012202 on Jan. 3, 2020, now abandoned.

(60) Provisional application No. 62/788,916, filed on Jan. 6, 2019.

(51) Int. Cl.
*A61K 38/48* (2006.01)
*A61K 31/7016* (2006.01)
*A61P 17/00* (2006.01)

(52) U.S. Cl.
CPC ...... *A61K 38/4886* (2013.01); *A61K 31/7016* (2013.01); *A61P 17/00* (2018.01); *C12Y 304/24003* (2013.01); *C12Y 304/24007* (2013.01)

(58) Field of Classification Search
CPC ............ A61K 38/4886; A61K 31/7016; A61K 2300/00; A61K 9/08; A61K 9/19; A61K 47/10; A61K 47/18; A61K 47/26; A61P 17/00; C12Y 304/24003; C12Y 304/24007
See application file for complete search history.

(56) References Cited

U.S. PATENT DOCUMENTS

| | | | |
|---|---|---|---|
| 7,811,560 B2 | 10/2010 | Sabatino et al. | |
| 9,744,138 B2 | 8/2017 | Leppert et al. | |
| 9,757,435 B2 | 9/2017 | Herber | |
| 2002/0192207 A1 | 12/2002 | Kendrick | |
| 2004/0116345 A1 | 6/2004 | Besman et al. | |
| 2006/0263347 A1 | 11/2006 | Kendrick et al. | |
| 2007/0237758 A1 | 10/2007 | Barry et al. | |
| 2011/0033464 A1 | 2/2011 | Barry et al. | |
| 2014/0335072 A1* | 11/2014 | Hart | A61K 38/4886 424/94.67 |
| 2017/0333536 A1 | 11/2017 | Jain | |
| 2018/0099049 A1 | 4/2018 | Tang et al. | |

FOREIGN PATENT DOCUMENTS

| | | |
|---|---|---|
| CN | 101312744 A | 11/2008 |
| JP | 2003-510369 A | 3/2003 |
| JP | 2003-520764 A | 7/2003 |
| JP | 2009-516692 A | 4/2009 |
| JP | 2014-530873 A | 11/2014 |
| WO | 2007/100675 A2 | 9/2007 |
| WO | 2012/125948 A1 | 9/2012 |
| WO | 2013/059619 A1 | 4/2013 |
| WO | 2018/160905 A1 | 9/2018 |

OTHER PUBLICATIONS

Johnson RE, Kirchhoff CF, Gaud HT. Mannitol-sucrose mixtures—versatile formulations for protein lyophilization. J Pharm Sci. Apr. 2002;91(4):914-22. doi: 10.1002/jps.10094. PMID: 11948529. (Year: 2002).*

Passot et al. / European Journal of Pharmaceutics and Biopharmaceutics 60 (2005) 335-348. (Year: 2005).*

Tang et al., Pharmaceutical Research, 2004, vol. 21, No. 2, p. 191-200. (Year: 2004).*

* cited by examiner

*Primary Examiner* — Kade Ariani

(74) *Attorney, Agent, or Firm* — BakerHostetler

(57) ABSTRACT

Disclosed herein are improved collagenase-containing formulations and methods of preparing the same. The collagenase-containing formulations comprise a collagenase, about 30 mM to about 240 mM of a disaccharide, about 50 mM to about 800 mM of mannitol, and about 6 mM to about 10 mM of a Tris-HCl. Lyophilized and reconstituted formulations are also provided.

9 Claims, 11 Drawing Sheets
Specification includes a Sequence Listing.

Bottom of a Lyo-cake of Va, 50x magnification

Bottom of a Lyo-cake of Va, 150x magnification

Cross-section of a Lyo-cake of Va, 50x magnification

Cross-section of a Lyo-cake of Va, 150x magnification

Top surface of a Lyo-cake of Va, 50x magnification

Top surface of a Lyo-cake of Va, 150x magnification

Bottom of a Lyo-cake of Vb, 50x magnification

Bottom of a Lyo-cake of Vb, 150x magnification

Cross-section of a Lyo-cake of Vb, 50x magnification

Cross-section of a Lyo-cake of Vb, 150x magnification

Top surface of a Lyo-cake of Vb, 50x magnification

Top surface of a Lyo-cake of Vb, 150x magnification

Bottom of a Lyo-cake of Vc, 50x magnification

Bottom of a Lyo-cake of Vc, 150x magnification

Cross-section of a Lyo-cake of Vc, 50x magnification

Cross-section of a Lyo-cake of Vc, 150x magnification

Top surface of a Lyo-cake of Vc, 50x magnification

Top surface of a Lyo-cake of Vc, 150x magnification

Appearance at a vacuum of 128 μbar

From Left to Right: Formulation 5, 3 and 1

Appearance at a vacuum of 380 μbar

From Left to Right: Formulation 5, 3 and 1

Appearance at a vacuum of 1030 μbar

From Left to Right: Formulation 5, 3 and 1

Appearance at a vacuum of 128 µbar

From Left to Right: Formulation 5 and 3

Appearance at a vacuum of 4000 µbar

From Left to Right: Formulation 5 and 3

SEQUENCE LISTING

```
Sequence total quantity: 2
SEQ ID NO: 1            moltype = AA   length = 1008
FEATURE                 Location/Qualifiers
source                  1..1008
                        mol_type = protein
                        organism = Clostridium histolyticum
SEQUENCE: 1
IANTNSEKYD FEYLNGLSYT ELTNLIKNIK WNQINGLFNY STGSQKFFGD KNRVQAIINA   60
LQESGRTYTA NDMKGIETFT EVLRAGFYLG YYNDGLSYLN DRNFQDKCIP AMIAIQKNPN  120
FKLGTAVQDE VITSLGKLIG NASANAEVVN NCVPVLKQFR ENLNQYAPDY VKGTAVNELI  180
KGIEFDFSGA AYEKDVKTMP WYGKIDPFIN ELKALGLYGN ITSATEWASD VGIYYLSKFG  240
LYSTNRNDIV QSLEKAVDMY KYGKIAFVAM ERITWDYDGI GSNGKKVDHD KFLDDAEKHY  300
LPKTYTFDNG TFIIRAGEKV SEEKIKRLYW ASREVKSQFH RVVGNDKALE VGNADDVLTM  360
KIFNSPEEYK FNTNINGVST DNGGLYIEPR GTFYTYERTP QQSIFSLEEL FRHEYTHYLQ  420
ARYLVDGLWG QGPFYEKNRL TWFDEGTAEF FAGSTRTSGV LPRKSILGYL AKDKVDHRYS  480
LKKTLNSGYD DSDWMFYNYG FAVAHYLYEK DMPTFIKMNK AILNTDVKSY DEIIKKLSDD  540
ANKNTEYQNH IQELADKYQG AGIPLVSDDY LKDHGYKKAS EVYSEISKAA SLTNTSVTAE  600
KSQYFNTFTL RGTYTGETSK GEFKDWDEMS KKLDGTLESL AKNSWSGYKT LTAYFTNYRV  660
TSDNKVQYDV VFHGVLTDNA DISNNKAPIA KVTGPSTGAV GRNIEFSGKD SKDEDGKIVS  720
YDWDFGDGAT SRGKNSVHAY KKTGTYNVTL KVTDDKGATA TESFTIEIKN EDTTTPITKE  780
```

```
MEPNDDIKEA NGPIVEGVTV KGDLNGSDDA DTFYFDVKED GDVTIELPYS GSSNFTWLVY  840
KEGDDQNHIA SGIDKNNSKV GTFKATKGRH YVFIYKHDSA SNISYSLNIK GLGNEKLKEK  900
ENNDSSDKAT VIPNFNTTMQ GSLLGDDSRD YYSFEVKEEG EVNIELDKKD EFGVTWTLHP  960
ESNINDRITY GQVDGNKVSN KVKLRPGKYY LLVYKYSGSG NYELRVNK              1008

SEQ ID NO: 2            moltype = AA  length = 991
FEATURE                 Location/Qualifiers
source                  1..991
                        mol_type = protein
                        organism = Clostridium histolyticum
SEQUENCE: 2
AVDKNNATAA VQNESKRYTV SYLKTLNYYD LVDLLVKTEI ENLPDLFQYS SDAKEFYGNK  60
TRMSFIMDEI GRRAPQYTEI DHKGIPTLVE VVRAGFYLGF HNKELNEINK RSFKERVIPS  120
ILAIQKNPNF KLGTEVQDKI VSATGLLAGN ETAPPEVVNN FTPIIQDCIK NMDRYALDDL  180
KSKALFNVLA APTYDITEYL RATKEKPENT PWYGKIDGFI NELKKLALYG KINDNNSWII  240
DNGIYHIAPL GKLHSNNKIG IETLTEVMKI YPYLSMQHLQ SADQIERHYD SKDAEGNKIP  300
LDKFKKEGKE KYCPKTYTFD DGKVIIKAGA RVEEEKVKRL YWASKEVNSQ FFRVYGIDKP  360
LEEGNPDDIL TMVIYNSPEE YKLNSVLYGY DTNNGGMYIE PDGTFFTYER KAEESTYTLE  420
ELFRHEYTHY LQGRYAVPGQ WGRTKLYDND RLTWYEEGGA ELFAGSTRTS GILPRKSIVS  480
NIHNTTRNNR YKLSDTVHSK YGASFEFYNY ACMFMDYMYN KDMGILNKLN DLAKNNDVDG  540
YDNYIRDLSS NHALNDKYQD HMQERIDNYE NLTVPFVADD YLVRHAYKNP NEIYSEISEV  600
AKLKDAKSEV KKSQYFSTFT LRGSYTGGAS KGKLEDQKAM NKFIDDSLKK LDTYSWSGYK  660
TLTAYFTNYK VDSSNRVTYD VVFHGYLPNE GDSKNSLPYG KINGTYKGTE KEKIKFSSEG  720
SFDPDGKIVS YEWDFGDGNK SNEENPEHSY DKVGTYTVKL KVTDDKGESS VSTTTAEIKD  780
LSENKLPVIY MHVPKSGALN QKVVFYGKGT YDPDGSIAGY QWDFGDGSDF SSEQNPSHVY  840
TKKGEYTVTL RVMDSSGQMS EKTMKIKITD PVYPIGTEKE PNNSKETASG PIVPGIPVSG  900
TIENTSDQDY FYFDVITPGE VKIDINKLGY GGATWVVYDE NNNAVSYATD DGQNLSGKFK  960
ADKPGRYYIH LYMFNGSYMP YRINIEGSVG R                                991
```

COLLAGENASE FORMULATIONS AND METHODS OF PRODUCING THE SAME

CROSS REFERENCE TO RELATED APPLICATIONS

This application is a continuation of U.S. application Ser. No. 17/419,899, filed on Jun. 30, 2021, which is the U.S. National Stage Application of International Patent Application No. PCT/US2020/012202, filed on Jan. 3, 2020, which claims priority to U.S. Provisional Application No. 62/788,916, filed on Jan. 6, 2019, the disclosures of each of which are hereby incorporated by reference in their entirety.

REFERENCE TO A SEQUENCE LISTING

This application includes a Sequence Listing submitted electronically in XML format. The XML copy, created on Oct. 6, 2023, is named 117326_000554_Sequence listing.xml and is 4,861 bytes in size. The Sequence Listing is incorporated by reference in its entirety herein.

FIELD OF THE INVENTION

Disclosed herein are collagenase-comprising formulations with improved stability and storage properties.

BACKGROUND OF THE INVENTION

XIAFLEX® (collagenase from *Clostridium histolyticum* (CCH)) is currently approved for the treatment of Dupuytren's Contracture (DC) and Peyronie's Disease (PD). The currently approved XIAFLEX® formulation is supplied as a lyophilized cake containing 0.9 mg CCH in 3CC vials along with a diluent vial. The current XIAFLEX® formulation (pre-lyophilization) has a lyophilization cycle time of about 72 hours in vials. Efficient lyophilization is required for shelf life and enzyme stability.

SUMMARY OF THE INVENTION

Disclosed herein are formulations comprising: a collagenase; about 30 mM to about 240 mM of a disaccharide; about 50 mM to about 800 mM of mannitol; and about 6 mM to about 10 mM of a Tris-HCl.

Also provided herein are lyophilized formulations comprising: a collagenase; a disaccharide; mannitol; and Tris-HCl.

Reconstituted formulations comprising: a collagenase; a disaccharide; mannitol; Tris-HCl; calcium chloride; and sodium chloride are also disclosed.

Kits are also provided, wherein the kits comprise: a container comprising any of the disclosed lyophilized formulations; and a container comprising a sterile diluent comprising calcium chloride and sodium chloride.

BRIEF DESCRIPTION OF THE DRAWINGS

The summary, as well as the following detailed description, is further understood when read in conjunction with the appended drawings. For the purpose of illustrating the disclosed formulations, there are shown in the drawings exemplary embodiments of the formulations; however, the formulations are not limited to the specific embodiments disclosed. In the drawings.

DETAILED DESCRIPTION OF ILLUSTRATIVE EMBODIMENTS

Figure 1:
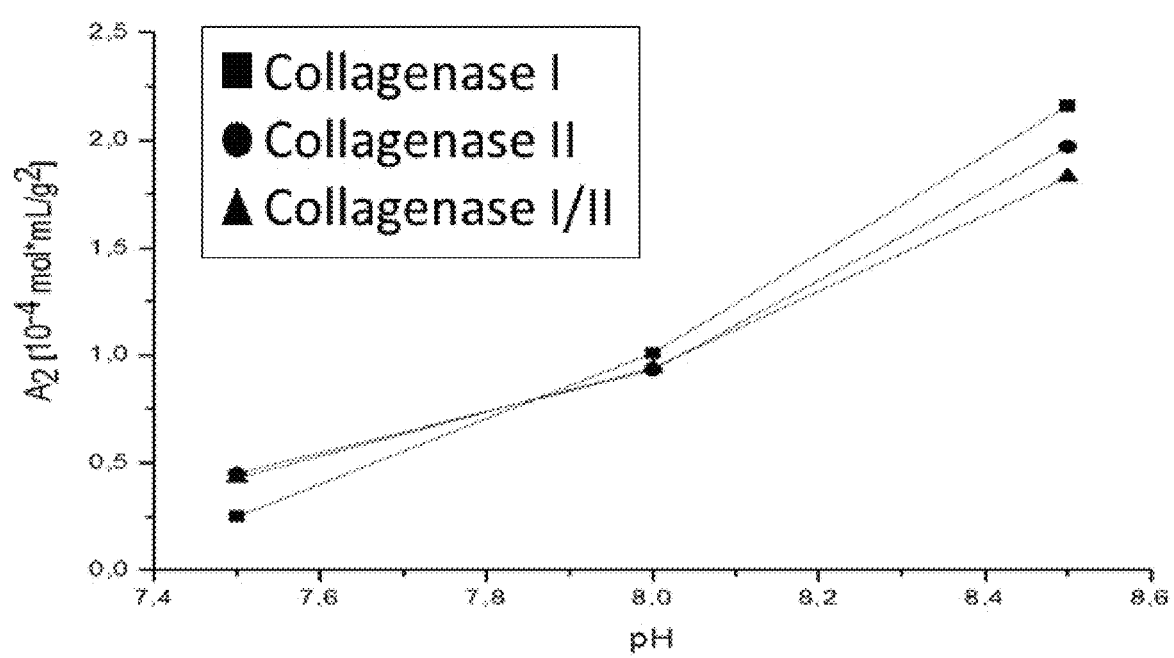
FIG. 1 illustrates the effect of pH on protein interactions in exemplary formulations comprising trehalose, mannitol, and various collagenases.

The disclosed formulations may be understood more readily by reference to the following detailed description taken in connection with the accompanying figures, which form a part of this disclosure. It is to be understood that the disclosed formulations are not limited to the specific formulations described and/or shown herein, and that the terminology used herein is for the purpose of describing particular embodiments by way of example only and is not intended to be limiting of the claimed formulations.

Unless specifically stated otherwise, any description as to a possible mechanism or mode of action or reason for improvement is meant to be illustrative only, and the disclosed formulations are not to be constrained by the correctness or incorrectness of any such suggested mechanism or mode of action or reason for improvement.

Throughout this text, the descriptions refer to formulations and methods of preparing the formulations. Where the disclosure describes or claims a feature or embodiment associated with a formulation, such a feature or embodiment is equally applicable to the methods of forming the formulation. Likewise, where the disclosure describes or claims a feature or embodiment associated with a method of forming a formulation, such a feature or embodiment is equally applicable to the formulation.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the disclosure be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed formulations which are, for clarity, described herein in the context of separate embodiments, may also be provided in combination in a single embodiment. Conversely, various features of the disclosed formulations that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of."

The following abbreviations are used herein: collagenase *Clostridium histolyticum* (CCH), United States Pharmacopeia (USP), Nephelometric Turbidity Units (NTU), Polysorbate (PS), Hydrogen peroxide ($H_2O_2$).

Provided herein are formulations comprising, or consisting of:

a collagenase;
about 30 mM to about 240 mM of a disaccharide;
about 50 mM to about 800 mM of mannitol; and
about 6 mM to about 10 mM of a Tris-HCl.

The formulations can contain between about 0.2 mg/ml to about 50 mg/ml of collagenase. For example, the lyophilized formulation can contain about 0.2 mg/ml, about 0.3 mg/ml, about 0.4 mg/ml, about 0.6 mg/ml, about 0.8 mg/ml, about 0.9 mg/ml, about 1 mg/ml, about 1.2 mg/ml, about 1.4 mg/ml, about 1.6 mg/ml, about 1.8 mg/ml, about 2 mg/ml, about 2.5 mg/ml, about 3 mg/ml, about 3.5 mg/ml, about 4 mg/ml, about 4.5 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, or about 50 mg/ml of collagenase.

As used herein, "collagenase" refers to any of the following: (a) collagenase (including mutants) having activity as defined by EC 3.4.24.3 (www.brenda-enzymes.org/enzyme.php?ecno=3.4.24.3 (accessed Jul. 3, 2019); (b) collagenase produced by fermentation of *Clostridium histolyticum* (also known as *Hathewaya histolytica*); (c) CCH (as described herein); (d) collagenase having at least 50% sequence alignment with collagenase I (also referred as class I collagenase) as determined by BLAST; (e) collagenase having at least 50% sequence alignment with collagenase II (also referred as class II collagenase) as determined by BLAST; (f) collagenase produced by fermentation of other source organisms (i.e., non-*Clostridium histolyticum*), e.g., mammalian, crustacean, fungal, bacterial or microbial collagenase; (g) collagenase obtained by recombinant techniques; (h) collagenase with a molecular mass from about 65 kDa to about 130 kDa; (i) collagenase designated as collagenase I or collagenase II; (j) mixtures of collagenase I and II; (k) collagenase from strain JCM 1403 (ATCC 19401) or derivatives thereof; (l) collagenase from strain ATCC 21000 or derivatives thereof; (m) collagenase from ATCC 69334 or derivatives thereof; (n) collagenase from *C. perfringens*; (o) collagenase from *Vibrio alginolyticus*; (p) collagenase from *Streptomyces*; (q) collagenase from *Pseudomonas*; (r) collagenase from *Achromobacter iophagus*; (s) collagenase described by Worthington Biochemical Corp. (www.Worthington-biochem.com; "Product Highlights"); (t) collagenase described by Sigma-Aldrich (www.sigma-aldrich.com); (u) collagenase having one or more of the following characteristics:

$V_{max}$ (min$^{-1}$) of about 0.08 to 7.70 (SRC assay), or about 0.3 to 30.5 (GPA assay);

$K_M$, of about 4.1 to 410 nM (SRC assay), or about 0.03 to 3.1 mM (GPA assay);

$K_{cat}$ (sec$^{-1}$) of about 1.1 to 107 (SRC assay), or about 93 to 9,179 (GPA assay);

$1/K_{cat}$, microseconds of about 376 to 37,222 (SRC assay), or about 4 to 428 (GPA assay); or $K_{cat}/K_M$, mM$^{-1}$sec$^{-1}$ of about 5,140 to 508,814 (SRC assay), or about 60 to 5,934 (GPA assay);

(v) collagenase described by Nordmark Arzneimittel GmbH & Co. KG; (w) collagenase from strain 004; or (x) equivalents or mixtures of any of the foregoing. Non-limiting examples of collagenases that may be used in the disclosure herein are described in U.S. Pat. Nos. 7,811,560, 9,757,435, 9,744,138, and Int'l Pub. No. WO2012/125948.

In some embodiments the collagenase can comprise a collagenase I. A suitable collagenase I includes, for example, a collagenase I comprising an amino acid sequence that is 90%, 91%, 92%, 93%, 94%, 95%, 96%, 97%, 98%, 99%, or 100% identical to the amino acid sequence of SEQ ID NO: 1. In some aspects, the collagenase I comprises the amino acid sequence of SEQ ID NO: 1.

In some embodiments, the collagenase can comprise a collagenase II. A suitable collagenase II includes, for example, a collagenase II comprising an amino acid sequence that is 90%, 91%, 92%, 93%, 94%, 95%, 96%, 97%, 98%, 99%, or 100% identical to the amino acid sequence of SEQ ID NO: 2. In some aspects, the collagenase II comprises the amino acid sequence of SEQ ID NO: 2.

TABLE 1

| | Sequences |
|---|---|
| Collagenase I (SEQ ID NO: 1) | IANTNSEKYDFEYLNGLSYTELTNL IKNIKWNQINGLFNYSTGSQKFFGD KNRVQAIINALQESGRTYTANDMKG IETFTEVLRAGFYLGYYNDGLSYLN DRNFQDKCIPAMIAIQKNPNFKLGT AVQDEVITSLGKLIGNASANAEVVN NCVPVLKQFRENLNQYAPDYVKGTA VNELIKGIEFDFSGAAYEKDVKTMP WYGKIDPFINELKALGLYGNITSAT EWASDVGIYYLSKFGLYSTNRNDIV QSLEKAVDMYKYGKIAFVAMERITW DYDGIGSNGKKVDHDKELDDAEKHY LPKTYTEDNGTFIIRAGEKVSEEKI KRLYWASREVKSQFHRVVGNDKALE VGNADDVLTMKIENSPEEYKENTNI NGVSTDNGGLYIEPRGTFYTYERTP QQSIFSLEELFRHEYTHYLQARYLV DGLWGQGPFYEKNRLTWFDEGTAEF FAGSTRTSGVLPRKSILGYLAKDKV |

TABLE 1-continued

Sequences

| | |
|---|---|
| | DHRYSLKKTLNSGYDDSDWMFYNYG<br>FAVAHYLYEKDMPTFIKMNKAILNT<br>DVKSYDEIIKKLSDDANKNTEYQNH<br>IQELADKYQGAGIPLVSDDYLKDHG<br>YKKASEVYSEISKAASLTNTSVTAE<br>KSQYFNTFTLRGTYTGETSKGEFKD<br>WDEMSKKLDGTLESLAKNSWSGYKT<br>LTAYFTNYRVTSDNKVQYDVVFHGV<br>LTDNADISNNKAPIAKVTGPSTGAV<br>GRNIEFSGKDSKDEDGKIVSYDWDF<br>GDGATSRGKNSVHAYKKTGTYNVTL<br>KVTDDKGATATESFTIEIKNEDTTT<br>PITKEMEPNDDIKEANGPIVEGVTV<br>KGDLNGSDDADTFYFDVKEDGDVTI<br>ELPYSGSSNFTWLVYKEGDDQNHIA<br>SGIDKNNSKVGTFKATKGRHYVFIY<br>KHDSASNISYSLNIKGLGNEKLKEK<br>ENNDSSDKATVIPNFNTTMQGSLLG<br>DDSRDYYSFEVKEEGEVNIELDKKD<br>EFGVTWTLHPESNINDRITYGQVDG<br>NKVSNKVKLRPGKYYLLVYKYSGSG<br>NYELRVNK |
| Collagenase II<br>(SEQ ID NO: 2) | AVDKNNATAAVQNESKRYTVSYLKT<br>LNYYDLVDLLVKTEIENLPDLFQYS<br>SDAKEFYGNKTRMSFIMDEIGRRAP<br>QYTEIDHKGIPTLVEVVRAGFYLGF<br>HNKELNEINKRSFKERVIPSILAIQ<br>KNPNFKLGTEVQDKIVSATGLLAGN<br>ETAPPEVVNNFTPIIQDCIKNMDRY<br>ALDDLKSKALFNVLAAPTYDITEYL<br>RATKEKPENTPWYGKIDGFINELKK<br>LALYGKINDNNSWIIDNGIYHIAPL<br>GKLHSNNKIGIETLTEVMKIYPYLS<br>MQHLQSADQIERHYDSKDAEGNKIP<br>LDKFKKEGKEKYCPKTYTFDDGKVI<br>IKAGARVEEEKVKRLYWASKEVNSQ<br>FFRVYGIDKPLEEGNPDDILIMVIY<br>NSPEEYKLNSVLYGYDTNNGGMYIE<br>PDGTFFTYERKAEESTYTLEELFRH<br>EYTHYLQGRYAVPGQWGRTKLYDND<br>RLTWYEEGGAELFAGSTRTSGILPR<br>KSIVSNIHNTTRNNRYKLSDTVHSK<br>YGASFEFYNYACMFMDYMYNKDMGI<br>LNKLNDLAKNNDVDGYDNYIRDLSS<br>NHALNDKYQDHMQERIDNYENLTVP<br>FVADDYLVRHAYKNPNEIYSEISEV<br>AKLKDAKSEVKKSQYFSTFTLRGSY<br>TGGASKGKLEDQKAMNKFIDDSLKK<br>LDTYSWSGYKTLTAYFTNYKVDSSN<br>RVTYDVVFHGYLPNEGDSKNSLPYG<br>KINGTYKGTEKEKIKFSSEGSFDPD<br>GKIVSYEWDFGDGNKSNEENPEHSY<br>DKVGTYTVKLKVTDDKGESSVSTTT<br>AEIKDLSENKLPVIYMHVPKSGALN<br>QKVVFYGKGTYDPDGSIAGYQWDFG<br>DGSDFSSEQNPSHVYTKKGEYTVTL<br>RVMDSSGQMSEKTMKIKITDPVYPI<br>GTEKEPNNSKETASGPIVPGIPVSG<br>TIENTSDQDYFYFDVITPGEVKIDI<br>NKLGYGGATWVVYDENNNAVSYATD<br>DGQNLSGKFKADKPGRYYIHLYMFN<br>GSYMPYRINIEGSVGR |

In some embodiments, the collagenase can comprise a mixture of collagenase I and collagenase II. The collagenase can comprise, for example, a mixture of a collagenase I comprising an amino acid sequence that is 90%, 91%, 92%, 93%, 94%, 95%, 96%, 97%, 98%, 99%, or 100% identical to the amino acid sequence of SEQ ID NO: 1 and a collagenase II comprising an amino acid sequence that is 90%, 91%, 92%, 93%, 94%, 95%, 96%, 97%, 98%, 99%, or 100% identical to the amino acid sequence of SEQ ID NO: 2. In some aspects, the collagenase comprises a mixture of the collagenase I comprising the amino acid sequence of SEQ ID NO: 1 and the collagenase II comprising the amino acid sequence of SEQ ID NO: 2. Suitable mixtures of the collagenase I and collagenase II include, for example, a collagenase I:collagenase II mass ratio of 0.1:1, 0.25:1, 0.5:1, 0.75:1, 1:1, 1.1:1, 1.25:1, 1.5:1, 1.75:1, 2:1, 1:0.1, 1:0.25, 1:0.5; 1:0.75, 1:1.1, 1:1.25, 1:1.5, 1:1.75, or 1:2. Each of the collagenase I and collagenase II may have a purity of at least 80%, 85%, 90%, 91%, 92%, 93%, 94%, 95%, 96%, 97%, 98%, 99%, or 100% as measured by, for example, reverse phase HPLC.

In some embodiments, the collagenase can comprise collagenase *Clostridium histolyticum* (CCH). "CCH," as used herein, refers to collagenase *Clostridium histolyticum* containing a mixture of collagenase I (SEQ ID NO: 1) and collagenase II (SEQ ID NO: 2) in an approximate 1:1 mass ratio. CCH is obtained by the fermentation of *Clostridium histolyticum* (also known as *Hathewaya histolytica*).

Suitable disaccharides include those that:
Stabilize proteins;
Protect proteins during both freezing and dehydration;
Inhibit lyophilization-induced unfolding;
Are non-reducing; and/or
Tend to remain amorphous during lyophilization.

In some embodiments, the disaccharide comprises sucrose or trehalose. In some aspects, the formulation comprises: a collagenase; about 30 mM to about 240 mM sucrose; about 50 mM to about 800 mM of mannitol; and about 6 mM to about 10 mM of a Tris-HCl. In some aspects, the formulation comprises: a collagenase; about 30 mM to about 240 mM of trehalose; about 50 mM to about 800 mM of mannitol; and about 6 mM to about 10 mM of a Tris-HCl.

The disaccharide can be present at a concentration of about 30 mM to about 240 mM, about 60 mM to about 240 mM, about 90 mM to about 240 mM, about 120 mM to about 240 mM, about 150 mM to about 240 mM, about 180 mM to about 240 mM, about 210 mM to about 240 mM, about 30 mM to about 210 mM, about 30 mM to about 180 mM, about 30 mM to about 150 mM, about 30 mM to about 120 mM, about 30 mM to about 90 mM, or about 30 mM to about 60 mM. The disaccharide can be present at a concentration of about 30 mM, 60 mM, 90 mM, 120 mM, 150 mM, 180 mM, 210 mM, or 240 mM.

The mannitol can be present at a concentration of about 50 mM to about 800 mM, about 100 mM to about 800 mM, about 150 mM to about 800 mM, about 200 mM to about 800 mM, about 250 mM to about 800 mM, about 300 mM to about 800 mM, about 350 mM to about 800 mM, about 400 mM to about 800 mM, about 450 mM to about 800 mM, about 500 mM to about 800 mM, about 550 mM to about 800 mM, about 600 mM to about 800 mM, about 650 mM to about 800 mM, about 700 mM to about 800 mM, about 750 mM to about 800 mM, about 50 mM to about 750 mM, about 50 mM to about 700 mM, about 50 mM to about 650 mM, about 50 mM to about 600 mM, about 50 mM to about 550 mM, about 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 150 mM, or about 50 mM to about 100 mM. The mannitol can be present at a concentration of about 50 mM, 100 mM, 150 mM, 200 mM, 225 mM, 250 mM, 300 mM, 350 mM, 400 mM, 450 mM, 500 mM, 550 mM, 600 mM, 650 mM, 700 mM, 750 mM, or 800 mM.

The pH of the formulation can be about 7.8 to about 8.8. The pH can be about 7.8, about 7.9, about 8.0, about 8.1, about 8.2, about 8.3, about 8.4, about 8.5, about 8.6, about 8.7, or about 8.8.

The formulation can comprise: CCH; about 60 mM sucrose; about 225 mM mannitol; and about 10 mM Tris-HCl, wherein the formulation has a pH of about 8.5. The formulation can comprise: about 0.9 mg CCH/ml; about 60 mM sucrose; about 225 mM mannitol; and about 10 mM Tris-HCl, wherein the formulation has a pH of about 8.5.

The formulation can consist of: CCH; about 60 mM sucrose; about 225 mM mannitol; and about 10 mM Tris-HCl, wherein the formulation has a pH of about 8.5. The formulation can consist of: about 0.9 mg CCH/ml; about 60 mM sucrose; about 225 mM mannitol; and about 10 mM Tris-HCl, wherein the formulation has a pH of about 8.5.

The disclosed formulation can further comprise a surfactant. Suitable surfactants include, for example, polysorbate 20, polysorbate 80, or poloxamer 188. The surfactant can be present at a concentration of about 0.01% to about 2%, about 0.05% to about 2%, about 0.1% to about 2%, about 0.15% to about 2%, about 0.2% to about 2%, about 0.25% to about 2%, about 0.3% to about 2%, about 0.4% to about 2%, about 0.5% to about 2%, about 1% to about 2%, about 1.5% to about 2%, about 0.01% to about 1.5%, about 0.01% to about 1%, about 0.01% to about 0.5%, about 0.01% to about 0.1%, or about 0.01% to about 0.05%. The surfactant can be present at a concentration of about 0.01%, 0.02%, 0.03%, 0.04%, 0.05%, 0.1%, 0.2% 0.5%, 1%, 1.5%, or 2%. In some embodiments, the formulation further comprises polysorbate 20 at a concentration of about 0.02%. In some embodiments, the formulation further comprises polysorbate 80 at a concentration of about 0.02%. In some embodiments, the formulation further comprises poloxamer 80 at a concentration of about 0.02%.

The above formulations can be liquid.

The disclosed formulations can be lyophilized under more aggressive conditions compared to previous collagenase-containing formulations, such as XIAFLEX®. For example, the disclosed formulations can be lyophilized in shorter times, using higher pressures, and/or with fewer drying steps (e.g., single temperature drying), resulting in a lyophilized formulation that exhibits increased stability and that maintains acceptable collagenase activity upon reconstitution. As shown herein, the pH and mannitol lead to the formation of a more robust formulation that can subsequently undergo more aggressive lyophilization.

Also provided herein are lyophilized formulations. The lyophilized formulations can be formed by the lyophilization of any of the above formulations. In some embodiments, the lyophilized formulations comprise, or consist of:

a collagenase;
a disaccharide;
mannitol; and
Tris-HCl.

The lyophilized formulation can contain between about 0.2 mg to about 50 mg of collagenase. For example, the lyophilized formulation can contain about 0.2 mg, 0.4 mg, 0.6 mg, 0.8 mg, 0.9 mg, 1 mg, 1.2 mg, 1.4 mg, 1.6 mg, 1.8 mg, 2 mg, 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, or 50 mg of collagenase.

The collagenase can comprises a collagenase I. A suitable collagenase I includes, for example, a collagenase I comprising an amino acid sequence that is 90%, 91%, 92%, 93%, 94%, 95%, 96%, 97%, 98%, 99%, or 100% identical to the amino acid sequence of SEQ ID NO: 1. In some embodiments, the collagenase I comprises the amino acid sequence of SEQ ID NO: 1.

The collagenase can comprise a collagenase II. A suitable collagenase II includes, for example, a collagenase II comprising an amino acid sequence that is 90%, 91%, 92%, 93%, 94%, 95%, 96%, 97%, 98%, 99%, or 100% identical to the amino acid sequence of SEQ ID NO: 2. In some embodiments, the collagenase II comprises the amino acid sequence of SEQ ID NO: 2.

The collagenase can comprise a mixture of collagenase I and collagenase II. The collagenase can comprise, for example, a mixture of a collagenase I comprising an amino acid sequence that is 90%, 91%, 92%, 93%, 94%, 95%, 96%, 97%, 98%, 99%, or 100% identical to the amino acid sequence of SEQ ID NO: 1 and a collagenase II comprising an amino acid sequence that is 90%, 91%, 92%, 93%, 94%, 95%, 96%, 97%, 98%, 99%, or 100% identical to the amino acid sequence of SEQ ID NO: 2. In some embodiments, the collagenase comprises a mixture of the collagenase I comprising the amino acid sequence of SEQ ID NO: 1 and the collagenase II comprising the amino acid sequence of SEQ ID NO: 2. Suitable mixtures of the collagenase I and collagenase II include, for example, a collagenase I:collagenase II mass ratio of 0.1:1, 0.25:1, 0.5:1, 0.75:1, 1:1, 1.1:1, 1.25:1, 1.5:1, 1.75:1, 2:1, 1:0.1, 1:0.25, 1:0.5; 1:0.75, 1:1.1, 1:1.25, 1:1.5, 1:1.75, or 1:2. In some embodiments, the collagenase is collagenase *Clostridium histolyticum* (CCH).

Each of the collagenase I and collagenase II may have a purity of at least 80%, 85%, 90%, 91%, 92%, 93%, 94%, 95%, 96%, 97%, 98%, 99%, or 100% as measured by, for example, reverse phase HPLC.

Suitable disaccharides include, for example, sucrose or trehalose. In some embodiments, the lyophilized formulation comprises, or consists of, a collagenase, sucrose, mannitol, and Tris-HCl. In some embodiments, the lyophilized formulation comprises, or consists of, a collagenase, trehalose, mannitol, and Tris-HCl.

The lyophilized formulations can be in a unit-dose vial, multi-dose vial, cartridge, or syringe. The lyophilized formulation can contain between about 0.2 mg to about 50 mg of collagenase. For example, the lyophilized formulation can contain about 0.2 mg, 0.4 mg, 0.6 mg, 0.8 mg, 0.9 mg, 1 mg, 1.2 mg, 1.4 mg, 1.6 mg, 1.8 mg, 2 mg, 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, or 50 mg of collagenase. The vial, cartridge, or syringe can have a volume of 2 mL to 50 mL, such as 5 mL, 7.5 mL, 10 mL, 15 mL, 20 mL, 30 mL, 40 mL, or 50 mL. The vial, cartridge, or syringe can contain between about 0.2 mg to about 50 mg of collagenase. For example, the vial, cartridge, or syringe can contain about 0.2 mg, 0.4 mg, 0.6 mg, 0.8 mg, 1 mg, 1.2 mg, 1.4 mg, 1.6 mg, 1.8 mg, 2 mg, 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, or 50 mg of collagenase. The vial, cartridge, or syringe can contain between about 0.2 mg to about 50 mg of the lyophilized formulation. For example, the vial, cartridge, or syringe can contain about 0.2 mg, 0.4 mg, 0.6 mg, 0.8 mg, 1 mg, 1.2 mg, 1.4 mg, 1.6 mg, 1.8 mg, 2 mg, 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, or 50 mg of the lyophilized formulation.

Prior to lyophilization, the formulation can comprise, or consist of: a collagenase; about 30 mM to about 240 mM of a disaccharide; about 50 mM to about 800 mM of mannitol; and about 6 mM to about 10 mM of a Tris-HCl. Prior to lyophilization, the formulation can comprise, or consist of: about 0.9 mg collagenase/ml; about 30 mM to about 240 mM of a disaccharide; about 50 mM to about 800 mM of mannitol; and about 6 mM to about 10 mM of a Tris-HCl. Prior to lyophilization, the formulation can comprise, or consist of: CCH; 60 mM sucrose; 225 mM mannitol; 10 mM Tris-HCl, and have a pH of about 8.5. In some embodiments, prior to lyophilization, the formulation can comprise, or consist of: about 0.9 mg CCH/ml; 60 mM sucrose; 225 mM mannitol; 10 mM Tris-HCl, and have a pH of about 8.5.

The disclosed lyophilized formulations have increased stability compared to previous collagenase-containing formulations, such as XIAFLEX®. For example, the disclosed lyophilized formulations are stable at pressures above 380 μbar, above 400 μbar, above 450 μbar, above 500 μbar, above 550 μbar, above 600 μbar, above 650 μbar, above 700 μbar, above 750 μbar, above 800 μbar, above 850 μbar, above 900 μbar, above 950 μbar, above 1000 μbar, above 1500 μbar, above 2000 μbar, above 2500 μbar, above 3000 μbar, above 3500 μbar, or above 4000 μbar. In some embodiments, the lyophilized formulation is stable at a pressure of about 4000 μbar.

The disclosed lyophilized formulations also exhibit improved shelf life and storage conditions compared to previous collagenase-containing formulations. For example, the disclosed lyophilized formulations exhibit an extended shelf life at low temperatures, such as 2-8° C., and at elevated temperatures, such as room temperature (40° C./75% relative humidity). The disclosed lyophilized formulation can be stable at, for example:
(a) 2–8° C. for at least 36 months;
(b) 25° C./60% relative humidity for at least 36 months;
(c) 40° C./75% relative humidity for at least 6 months; or
(d) any combination of (a) to (c).

The disclosed lyophilized formulation can be formed by a method comprising: freezing the formulation at a temperature between about –25° C. and –55° C. to form a frozen formulation; and drying the frozen formulation at a temperature between about 25° C. and about 50° C. to form the lyophilized formulation. Suitable temperatures for the freezing step include about –25° C., –30° C., –35° C., –40° C., –45° C., –50° C., or –55° C. Suitable temperatures for the drying step include about 25° C., 30° C., 35° C., 40° C., 45° C., or 50° C.

It has been shown that the lyophilized formulations can be formed using a single temperature freezing step and a single temperature drying step. For example, the lyophilized formulation can be formed by a method comprising: freezing the formulation at a single temperature between about –25° C. and –55° C. to form a frozen formulation; and drying the frozen formulation at a single temperature between about 25° C. and about 50° C. to form the lyophilized formulation. The single temperature freezing step can be performed at a temperature between about –25° C. and about –55° C. For example, the single temperature freezing step can be performed at about –25° C., –30° C., –35° C., –40° C. –45° C., –50° C., or –55° C. The single temperature drying step can be performed at a temperature between about 25° C. and about 50° C. For example, the single temperature drying step can be performed at about 25° C., 30° C., 35° C., 40° C., 45° C. or 50° C. When the method is performed with a single temperature freezing step and a single temperature drying step, the method may further comprise a "ramp up" step between the freezing and drying to allow the lyophilizer to reach the suitable drying temperature.

The disclosed lyophilized formulations can be formed by a lyophilization method that is much faster than the lyophilization method used to form other collagenase-containing lyophilized formulations. The lyophilized formulation can be formed by a lyophilization method that is performed for less than 72 hours. In some embodiments, the methods can be performed for less than 30 hours. In some embodiments, the methods can be performed for less than 18 hours. In some embodiments, the method can be performed for about 15 hours to about 25 hours.

The disclosed lyophilized formulations can be formed by a lyophilization method that uses a much higher pressure than the lyophilization method used to form other collagenase-containing lyophilized formulations. The lyophilized formulation can be formed by a lyophilization method that is performed at a pressure of between about 380 μbar to about 4000 μbar. The disclosed methods can be performed at a pressure of between about 500 μbar to about 4000 μbar, between about 750 μbar to about 4000 μbar, between about 1000 μbar to about 4000 μbar. The disclosed methods can be performed at 380 μbar, 500 μbar, 750 μbar, 1000 μbar, 1500 μbar, 2000 μbar, 2500 μbar, 3000 μbar, 3500 μbar, or 4000 μbar.

The disclosed lyophilized formulations, once reconstituted, can be used to treat or reduce collagen-mediated conditions, including the severity of cellulite (also known as edematous fibrosclerotic panniculopathy (EFP)), Dupuytren's contracture (DC) with a palpable cord, or Peyronie's disease (PD) with a palpable plaque and curvature deformity of at least 30 degrees.

Also provided herein are reconstituted formulations comprising, or consisting of: a collagenase; a disaccharide; mannitol; Tris-HCl; calcium chloride; and sodium chloride.

The collagenase can comprise a collagenase I. A suitable collagenase I includes, for example, a collagenase I comprising an amino acid sequence that is 90%, 91%, 92%, 93%, 94%, 95%, 96%, 97%, 98%, 99%, or 100% identical to the amino acid sequence of SEQ ID NO: 1. In some embodiments, the collagenase I comprises the amino acid sequence of SEQ ID NO: 1. The collagenase can comprise a collagenase II. A suitable collagenase II includes, for example, a collagenase II comprising an amino acid sequence that is 90%, 91%, 92%, 93%, 94%, 95%, 96%, 97%, 98%, 99%, or 100% identical to the amino acid sequence of SEQ ID NO: 2. In some embodiments, the collagenase II comprises the amino acid sequence of SEQ ID NO: 2. The collagenase can comprise a mixture of collagenase I and collagenase II. The collagenase can comprise, for example, a mixture of a collagenase I comprising an amino acid sequence that is 90%, 91%, 92%, 93%, 94%, 95%, 96%, 97%, 98%, 99%, or 100% identical to the amino acid sequence of SEQ ID NO: 1 and a collagenase II comprising an amino acid sequence that is 90%, 91%, 92%, 93%, 94%, 95%, 96%, 97%, 98%, 99%, or 100% identical to the amino acid sequence of SEQ ID NO: 2. In some embodiments, the collagenase comprises a mixture of the collagenase I comprising the amino acid sequence of SEQ ID NO: 1 and the collagenase II comprising the amino acid sequence of SEQ ID NO: 2. Suitable mixtures of the collagenase I and collagenase II include, for example, a collagenase I:collagenase II mass ratio of 0.1:1, 0.25:1, 0.5:1, 0.75:1, 1:1, 1.1:1, 1.25:1, 1.5:1, 1.75:1, 2:1, 1:0.1, 1:0.25, 1:0.5; 1:0.75, 1:1.1, 1:1.25, 1:1.5, 1:1.75, or 1:2. In some embodiments, the collagenase is collagenase *Clostridium histolyticum* (CCH).

Each of the collagenase I and collagenase II may have a purity of at least 80%, 85%, 90%, 91%, 92%, 93%, 94%, 95%, 96%, 97%, 98%, 99%, or 100% as measured by, for example, reverse phase HPLC.

Suitable disaccharides include, for example, sucrose or trehalose. In some embodiments, the reconstituted formulation comprises, or consists of, a collagenase, sucrose, mannitol, Tris-HCl, calcium chloride, and sodium chloride. In some embodiments, the lyophilized formulation comprises, or consists of, a collagenase, trehalose, mannitol, Tris-HCl, calcium chloride, and sodium chloride.

Suitable amounts of calcium chloride and sodium chloride include those that enable the reconstituted formulation to be isotonic to human blood. In some embodiments, the reconstituted formulation comprises about 0.01%, 0.02%, 0.03%, 0.04%, 0.05%, 0.06%, 0.07%, 0.09%, 0.1%, or greater than 0.1% of calcium chloride. In some embodiments, the reconstituted formulation comprises about 0.1%, 0.2%, 0.3%, 0.4%, 0.5%, 0.6%, 0.7%, 0.8%, 0.9%, 1%, or greater than 1% of sodium chloride.

The reconstituted formulation can also comprise water for injection (WFI).

The disclosed reconstituted formulations can be used to treat or reduce collagen-mediated conditions, including the severity of cellulite (also known as edematous fibrosclerotic panniculopathy (EFP)), Dupuytren's contracture (DC) with a palpable cord, or Peyronie's disease (PD) with a palpable plaque and curvature deformity of at least 30 degrees.

The reconstituted formulations can comprise about 0.01 mg to about 50 mg of the collagenase in a single or divided dose. The reconstituted formulation can comprise, for example, about 0.05 mg to about 15 mg, about 0.10 mg to about 10 mg, about 0.15 mg to about 5 mg, about 0.20 mg to about 3 mg, or about 0.25 mg to about 2 mg of the collagenase in a single or divided dose. The reconstituted formulation can comprise, for example, about 0.05 mg, about 0.10 mg, about 0.15 mg, about 0.20 mg, about 0.25 mg, about 0.30 mg, about 0.35 mg, about 0.40 mg, about 0.45 mg, about 0.50 mg, about 0.55 mg, about 0.60 mg, about 0.65 mg, about 0.70 mg, about 0.75 mg, about 0.80 mg, about 0.85 mg, about 0.90 mg, about 0.95 mg, about 1.00 mg, 1.05 mg, about 1.10 mg, about 1.15 mg, about 1.20 mg, about 1.25 mg, about 1.30 mg, about 1.35 mg, about 1.40 mg, about 1.45 mg, about 1.50 mg, about 1.55 mg, about 1.60 mg, about 1.65 mg, about 1.70 mg, about 1.75 mg, about 1.80 mg, about 1.85 mg, about 1.90 mg, about 1.95 mg, about 2.00 mg, 2.05 mg, about 2.10 mg, about 2.15 mg, about 2.20 mg, about 2.25 mg, about 2.30 mg, about 2.35 mg, about 2.40 mg, about 2.45 mg, about 2.50 mg, about 2.55 mg, about 2.60 mg, about 2.65 mg, about 2.70 mg, about 2.75 mg, about 2.80 mg, about 2.85 mg, about 2.90 mg, about 2.95 mg, about 3.00 mg, 3.05 mg, about 3.10 mg, about 3.15 mg, about 3.20 mg, about 3.25 mg, about 3.30 mg, about 3.35 mg, about 3.40 mg, about 3.45 mg, about 3.50 mg, about 3.55 mg, about 3.60 mg, about 3.65 mg, about 3.70 mg, about 3.75 mg, about 3.80 mg, about 3.85 mg, about 3.90 mg, about 3.95 mg, about 4.00 mg, 4.05 mg, about 4.10 mg, about 4.15 mg, about 4.20 mg, about 4.25 mg, about 4.30 mg, about 4.35 mg, about 4.40 mg, about 4.45 mg, about 4.50 mg, about 4.55 mg, about 4.60 mg, about 4.65 mg, about 4.70 mg, about 4.75 mg, about 4.80 mg, about 4.85 mg, about 4.90 mg, about 4.95 mg, about 5.00 mg, 5.05 mg, about 5.10 mg, about 5.15 mg, about 5.20 mg, about 5.25 mg, about 5.30 mg, about 5.35 mg, about 5.40 mg, about 5.45 mg, about 5.50 mg, about 5.55 mg, about 5.60 mg, about 5.65 mg, about 5.70 mg, about 5.75 mg, about 5.80 mg, about 5.85 mg, about 5.90 mg, about 5.95 mg, about 6.00 mg, about 10 mg, about 15 mg, about 20 mg, about 25 mg, about 30 mg, about 35 mg, about 40 mg, about 45 mg, or about 50 mg of the collagenase.

The reconstituted formulation can have a total volume of about 0.1 mL to about 50 mL. For example, the reconstituted formulation can have a total volume of about 0.1 mL, 0.2 mL, 0.3 mL, 0.4 mL, 0.5 mL, 1 mL, 1.5 mL, 2 mL, 2.5 mL, 3 mL, 3.5 mL, 4 mL, 4.5 mL, 5 mL, 10 mL, 15 mL, 20 mL, 25 mL, 30 mL, 35 mL, 40 mL, 45 mL, or 50 mL.

Kits comprising the disclosed lyophilized formulations and a sterile diluent are also provided. The kits can comprise: a container comprising any of the disclosed lyophilized formulations; and a container comprising a sterile diluent comprising calcium chloride and sodium chloride.

Suitable containers for the lyophilized formulation and/or the sterile diluent include, for example, a vial, cartridge, or syringe. The vial can be a unit-dose vial or a multi-dose vial. Suitable container sizes include, for example, 2 mL to 50 mL containers, such as 5 mL, 7.5 mL, 10 mL, 15 mL, 20 mL, 30 mL, 40 mL, or 50 mL.

The container comprising the disclosed lyophilized formulation can comprise between about 0.2 mg to about 50 mg collagenase. For example, the container can comprise about 0.2 mg, 0.4 mg, 0.6 mg, 0.8 mg, 1 mg, 1.2 mg, 1.4 mg, 1.6 mg, 1.8 mg, 2 mg, 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, or 50 mg collagenase. The container comprising the disclosed lyophilized formulation can comprise between about 0.2 mg to about 50 mg of the lyophilized formulation. For example, the container can comprise about 0.2 mg, 0.4 mg, 0.6 mg, 0.8 mg, 1 mg, 1.2 mg, 1.4 mg, 1.6 mg, 1.8 mg, 2 mg, 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, or 50 mg of the lyophilized formulation.

The container comprising the sterile diluent can comprise an amount of sterile diluent that, upon reconstitution of the lyophilized formulation, results in a solution that is isotonic to human blood. In some embodiments, the sterile diluent comprises about 0.01%, 0.02%, 0.03%, 0.04%, 0.05%, 0.06%, 0.07%, 0.08%, 0.09%, 0.1%, or greater than 0.1% of calcium chloride. In some embodiments, the sterile diluent comprises about 0.1%, 0.2%, 0.3%, 0.4%, 0.5%, 0.6%, 0.7%, 0.8%, 0.9%, 1%, or greater than 1% of sodium chloride.

The volume of the sterile diluent can be about 0.1 mL to about 50 mL. For example, the volume of the sterile diluent can be about 0.1 mL, 0.2 mL, 0.3 mL, 0.4 mL, 0.5 mL, 1 mL, 1.5 mL, 2 mL, 2.5 mL, 3 mL, 3.5 mL, 4 mL, 4.5 mL, 5 mL, 10 mL, 15 mL, 20 mL, 25 mL, 30 mL, 35 mL, 40 mL, 45 mL, or 50 mL.

Provided herein are methods of lyophilizing any of the disclosed formulations, the methods comprising: freezing the formulation at a temperature between about −25° C. and −55° C. to form a frozen formulation; and drying the frozen formulation at a temperature between about 25° C. and about 50° C. to form the lyophilized formulation.

In some embodiments, the freezing is performed at a single temperature and the drying is performed at a single temperature. In such embodiments, the methods may further comprise a "ramp up" step between the freezing and drying to allow the lyophilizer to reach the suitable drying temperature. The single temperature freezing step can be performed at a temperature between about −25° C. and about −55° C. For example, the single temperature freezing step can be performed at about −25° C., −30° C., −35° C., −40° C., −45° C., −50° C., or −55° C. The single temperature drying step can be performed at a temperature between about 25° C. and about 50° C. For example, the single temperature drying step can be performed at about 25° C., 30° C., 35° C., 40° C., 45° C., or 50° C.

The disclosed methods can be performed for less than 72 hours. In some embodiments, the methods can be performed for less than 30 hours. In some embodiments, the methods can be performed for less than 18 hours. In some embodiments, the method can be performed for about 15 hours to about 25 hours.

The disclosed methods can be performed at a pressure of between about 128 μbar to about 4000 μbar, between about 380 μbar to about 4000 μbar, between about 500 μbar to about 4000 μbar, between about 750 μbar to about 4000 μbar, between about 1000 μbar to about 4000 μbar. The disclosed methods can be performed at 380 μbar, 500 μbar, 750 μbar, 1000 μbar, 1500 μbar, 2000 μbar, 2500 μbar, 3000 μbar, 3500 μbar, or 4000 μbar.

Examples

The following examples are provided to further describe some of the embodiments disclosed herein. The examples are intended to illustrate, not to limit, the disclosed embodiments.

The XIAFLEX® formulation (CCH, 10 mM Tris/HCl pH 8.0, 60 mM sucrose) has a relatively long lyophilization cycle time of 72 hours. An objective of the below studies was to achieve a more efficient lyophilization process with reduced cycle time and improved yields.

The following criteria were considered during formulation and lyophilization process optimizations:

Formulation:
  pH that optimizes thermodynamic stability of protein;
  Trehalose or sucrose as cryoprotectant/lyoprotectant and to stabilize the protein;
  Addition of a bulking/isotonicity agent (e.g., mannitol); and
  Utilization of a nonionic surfactant to reduce protein aggregation, if necessary. Lyophilization Process:
  Inhibition of protein unfolding during freezing and drying;
  Glass transition temperature of the product to exceed the planned storage temperature;
  Ability to maintain a relatively low water content; and
  An elegant cake structure.

As a part of the work to identify an optimal formulation composition for lyophilization, several different solution formulations ("pre-lyophilization") containing various combinations of excipients such as sucrose, trehalose, and mannitol with and without surfactant at different levels were evaluated. In addition, untreated and siliconized (baked on) vials were also evaluated.

Formulation Robustness Studies—Study 1

The purpose of these studies was to challenge two formulation variants by freeze/thaw testing, sheer stress, thermal stress, peroxide stress and hydrophobic surface contact in comparison to the original XIAFLEX® formulation. The following formulations were exposed to thermal/shear stress and freeze/thaw stress test:

Variant A ($V_A$): CCH, 10 mM Tris/HCl pH 8.5, 60 mM trehalose, 225 mM mannitol
  Variant B ($V_B$): CCH, 10 mM Tris/HCl pH 8.0, 60 mM trehalose, 225 mM mannitol
  Original XIAFLEX® drug substance formulation (Or): CCH, 10 mM Tris/HCl pH 8.0, 60 mM sucrose Standard glass vials and siliconized glass vials were used for the test to investigate the influence of hydrophobic surfaces on the protein stability. The formulations were supplemented with two types of surfactants (polysorbate 20 and poloxamer 188) to examine the influence of surfactants on the stability of the formulations during the challenge testing. To force oxidative stress, the formulations were challenged in the presence of a strong oxidizing agent (hydrogen peroxide). In total, a matrix of 21 variants were used for the challenge testing.

Experimental Design

CCH was formulated in three different formulation variants. The formulation variants were exposed to thermal stress with agitation and freeze/thaw stress to challenge the formulation candidates. Hydrogen peroxide was added to the samples to force oxidative stress to the proteins. Each sample was analyzed after stress exposure by turbidity measurements to monitor the formation of aggregates.

Treatment of Glass Vials and Stoppers

Vials were washed in a laboratory dishwasher with purified water. Afterwards, the vials were dried and heat-treated at 300° C. for 2 hours for depyrogenization/sterilization. Stoppers were autoclaved at 2 bar and 121° C. for 20 min in sterilization bags and dried for 8 hours at 80° C.

Sample Preparation

First XIAFLEX® drug substance was dialyzed against the formulation variants A or B. The dialysis was accomplished in three independent dialysis steps to achieve a quantitative buffer exchange. 60 ml of the XIAFLEX® drug substance was dialyzed against formulation variant A and 40 ml of the XIAFLEX® drug substance was dialyzed against formulation variant B. XIAFLEX® drug substance was transferred into two preconditioned (in dialysis buffer) Slide-A-Lyzer™ cassettes (Thermo Scientific, Rockford, USA). Filled Slide-A-Lyzer™ cassettes were incubated in 2000 ml or 1000 ml of the target buffer for 2 hours before a first buffer change (2000 ml/1000 ml) was performed. After dialysis for two additional hours, the buffer was changed a second time (2000 ml for both formulation variants) to finalize the dialysis overnight. The protein sample was removed from the Slide-A-Lyzer™ cassettes and the concentration was adjusted to 1 mg/ml by dilution.

Addition of Detergents and Hydrogen Peroxide

After dialysis, the samples were supplemented with polysorbate 20, poloxamer 188, hydrogen peroxide, and combinations thereof by adding stock solutions (10% w/w polysorbate 20, 10% w/w poloxamer 188, 30% w/w $H_2O_2$). Variants of the original XIAFLEX® formulation were prepared by adding the detergents or hydrogen peroxide directly to the bulk solution. The composition of each variant is shown in Table 2:

TABLE 2

Formulation variants for the challenge testing

| # | Sample code | container | +PS20 0.02% | +P188 (0.1%) | +$H_2O_2$ (0.1%) |
|---|---|---|---|---|---|
| 1 | $V_A1$ | glass type 1 | | | |
| 2 | $V_A2$ | glass type 1 | X | | |
| 3 | $V_A3$ | glass type 1 | | X | |
| 4 | $V_A1s$ | silicon, glass | | | |
| 5 | $V_A2s$ | silicon, glass | X | | |
| 6 | $V_A3S$ | silicon, glass | | X | |
| 7 | $V_A4s$ | silicon, glass | | | X |
| 8 | $V_A5s$ | silicon, glass | X | | X |
| 9 | $V_A6s$ | silicon, glass | | X | X |
| 10 | $V_B1s$ | silicon, glass | | | |
| 11 | $V_B2s$ | silicon, glass | X | | |
| 12 | $V_B3s$ | silicon, glass | | X | |
| 13 | $V_B4s$ | silicon, glass | | | X |
| 14 | $V_B5s$ | silicon, glass | X | | X |
| 15 | $V_B6s$ | silicon, glass | | X | X |
| 16 | Or1s | silicon, glass | | | |
| 17 | Or2s | silicon, glass | X | | |
| 18 | Or3s | silicon, glass | | X | |
| 19 | Or4s | silicon, glass | | | X |

TABLE 2-continued

Formulation variants for the challenge testing

| # | Sample code | container | +PS20 0.02% | +P188 (0.1%) | +H$_2$O$_2$ (0.1%) |
|---|---|---|---|---|---|
| 20 | Or5s | silicon, glass | X | | X |
| 21 | Or6s | silicon, glass | | X | X |

Each formulation was sterile filtrated under laminar flow and exposed to thermal/agitation and freeze/thaw stress.

Freeze/Thaw Testing

The freeze/thaw stability of the formulations was tested by running 3 freeze/thaw cycles in total. Siliconized 6R glass vials or 2R standard glass vials were filled with 1.0 ml of each formulation. 3 vials were prepared for each variant. Liquid samples were frozen from 25° C. to −30° C. within 55 min at a controlled freezing rate and warmed up again to room temperature within 55 min at a controlled heating rate. For an adequate temperature control, the samples were loaded into a pilot freeze dryer. After each freeze/thaw cycle the turbidity of the samples was determined. For the turbidity measurement, 1 ml of each sample was filled in single-use turbidity cuvettes and analyzed. After analyzing, the liquid was returned to the glass vial and the experiment was continued.

Thermal Stress Test

Test samples of all formulations were stressed at 40° C. for 4 days under agitation (200 rpm) in 2R vials (1 ml fill volume). Turbidity of the stressed samples was analyzed afterwards.

Turbidity Measurement

The turbidity of the samples was determined using a 2100AN turbidity meter (Hach Lange, Dusseldorf, Germany) according to the European Pharmacopeia. The system was calibrated as follows:

Hydrazine sulphate solution: Dissolved 1.0 g of hydrazine sulphate in purified water and diluted to 100.0 ml with the same solvent. Allowed to stand for 4–6 h.

Hexamethylene tetramine solution: Dissolved 2.5 g of hexamethylene tetramine in 25.0 ml purified water in a 100 ml glass-toppered volumetric flask.

Primary opalescent suspension: Added 25.0 ml hydrazine sulphate solution to the hexamethylene tetramine solution in the volumetric flask. Mixed and allowed to stand for 24 h.

Standard of opalescence: Diluted 15.0 ml of the primary opalescent suspension to 1000.0 ml with purified water. This suspension was freshly prepared (stored for 24 h at most).

Reference suspensions: Prepared the reference suspensions according to Table 3.

TABLE 3

Preparation of the reference solution for the calibration of the turbidity meter.

| | I | II | III | IV |
|---|---|---|---|---|
| Standard of opalescence | 5.00 mL | 10.0 mL | 30.0 mL | 50.0 mL |
| Purified water | 95.0 mL | 90.0 mL | 70.0 mL | 50.0 mL |

Results and Discussion

Table 4 displays the result of the freeze/thaw testing. None of the variants showed an increase in turbidity with increasing number of freeze/thaw cycles. The enzymes seemed to be stable against freeze/thaw stress. The addition of surfactants or hydrogen peroxide showed no influence on the turbidity of the samples.

Table 5 shows the results of the thermal stress at 40° C. and agitation at 200 rpm. Variants containing hydrogen peroxide showed a clear increase of turbidity (as shown by the increased nephelometric turbidity units (NTU)) after thermal stress. In variants VA and variants VB (mannitol is present in both formulations) the resulting turbidity was remarkably lower (decreased NTU) than in the original XIAFLEX® formulation variant ("Or"—without mannitol). The beneficial effect of mannitol is believed to be caused by its radical scavenger properties.

TABLE 4

Results for the freeze/thaw challenge test

| # | Sample code | container | +PS20 0.02% | +P188 (0.1%) | +H$_2$O$_2$ (0.1%) | T0 | 1x F/T | 2x F/T | 3x F/T |
|---|---|---|---|---|---|---|---|---|---|
| 1 | V$_A$1 | glass type 1 | | | | 3.2 | 3.2 | 2.8 | 2.5 |
| 2 | V$_A$2 | glass type 1 | X | | | 3.3 | 2.7 | 2.3 | 2.7 |
| 3 | V$_A$3 | glass type 1 | | X | | 2.6 | 2.2 | 2.3 | 2.9 |
| 4 | V$_A$1s | silicon, glass | | | | 3.2 | 4.2 | 2.9 | 1.8 |
| 5 | V$_A$2s | silicon, glass | X | | | 3.3 | 2.7 | 2.5 | 2.3 |
| 6 | V$_A$3s | silicon, glass | | X | | 2.6 | 2.1 | 2.1 | 2.5 |
| 7 | V$_A$4s | silicon, glass | | | X | 2.9 | 3.5 | 2.6 | 3.0 |
| 8 | V$_A$5s | silicon, glass | X | | X | 2.0 | 2.3 | 2.2 | 2.6 |
| 9 | V$_A$6s | silicon, glass | | X | X | 2.6 | 2.5 | 2.5 | 2.5 |
| 10 | V$_B$1s | silicon, glass | | | | 1.9 | 2.5 | 2.4 | 2.7 |
| 11 | V$_B$2s | silicon, glass | X | | | 2.3 | 2.2 | 2.6 | 2.8 |
| 12 | V$_B$3s | silicon, glass | | X | | 3.0 | 2.5 | 2.6 | 3.1 |
| 13 | V$_B$4s | silicon, glass | | | X | 2.0 | 2.0 | 2.6 | 3.1 |
| 14 | V$_B$5s | silicon, glass | X | | X | 2.2 | 1.9 | 2.1 | 2.5 |
| 15 | V$_B$6s | silicon, glass | | X | X | 2.1 | 2.3 | 2.9 | 2.5 |
| 16 | Or1s | silicon, glass | | | | 2.3 | 1.9 | 1.9 | 3.0 |
| 17 | Or2s | silicon, glass | X | | | 2.7 | 2.4 | 2.5 | 2.9 |
| 18 | Or3s | silicon, glass | | X | | 2.2 | 2.9 | 2.4 | 2.7 |
| 19 | Or4s | silicon, glass | | | X | 2.0 | 2.8 | 2.7 | 3.0 |
| 20 | Or5s | silicon, glass | X | | X | 2.5 | 2.8 | 2.2 | 3.0 |
| 21 | Or6s | silicon, glass | | X | X | 1.8 | 3.2 | 2.3 | 2.4 |

TABLE 5

Results of the thermal challenge test

| Sample # | code | container | +PS20 0.02% | +P188 (0.1%) | +H$_2$O$_2$ (0.1%) | Turbidity [NTU] T0 | 4 days 40° C. + 200 rpm |
|---|---|---|---|---|---|---|---|
| 1 | V$_A$1 | glass type 1 | | | | 3.2 | 3.1 |
| 2 | V$_A$2 | glass type 1 | X | | | 3.3 | 2.5 |
| 3 | V$_A$3 | glass type 1 | | X | | 2.6 | 2.4 |
| 4 | V$_A$1s | silicon, glass | | | | 3.2 | 2.6 |
| 5 | V$_A$2s | silicon, glass | X | | | 3.3 | 2.5 |
| 6 | V$_A$3s | silicon, glass | | X | | 2.6 | 2.6 |
| 7 | V$_A$4s | silicon, glass | | | X | 2.9 | 7.0 |
| 8 | V$_A$5s | silicon, glass | X | | X | 2.0 | 6.2 |
| 9 | V$_A$6s | silicon, glass | | X | X | 2.6 | 6.3 |
| 10 | V$_B$1s | silicon, glass | | | | 1.9 | 2.7 |
| 11 | V$_B$2s | silicon, glass | X | | | 2.3 | 2.3 |
| 12 | V$_B$3s | silicon, glass | | X | | 3.0 | 1.9 |
| 13 | V$_B$4s | silicon, glass | | | X | 2.0 | 24.2 |
| 14 | V$_B$5s | silicon, glass | X | | X | 2.2 | 24.5 |
| 15 | V$_B$6s | silicon, glass | | X | X | 2.1 | 25.8 |
| 16 | Or1s | silicon, glass | | | | 2.3 | 2.1 |
| 17 | Or2s | silicon, glass | X | | | 2.7 | 2.5 |
| 18 | Or3s | silicon, glass | | X | | 2.2 | 2.9 |
| 19 | Or4s | silicon, glass | | | X | 2.0 | 44.8 |
| 20 | Or5s | silicon, glass | X | | X | 2.5 | 46.5 |
| 21 | Or6s | silicon, glass | | X | X | 1.8 | 54.7 |

Conclusions

The increase of turbidity differed significantly between Variant VA and VB. It is believed that higher repulsive interactions between the molecules at pH 8.5 compared to pH 8.0 reduced the tendency for aggregate formation caused by the oxidative stress.

The addition of surfactants showed neither a positive nor a negative effect on the turbidity of the samples. The hydrophobic surface of siliconized glass vials had no impact on the turbidity of the samples after thermal stress.

The samples were analyzed by turbidity measurements to monitor the formation of aggregates. The turbidity of the samples did not increase by freeze/thaw cycling. The formulations seemed to be stable against the formation of aggregates under freeze/thaw stress (up to 3 cycles). Hydrophobic surface contact as well as addition of hydrogen peroxide had no influence on the turbidity of the samples either with or without surfactants during freeze/thaw stress. Under thermal stress, a clear increase in turbidity (as measured by NTU) under forced oxidative stress was observed (addition of hydrogen peroxide). Variants containing mannitol and having higher repulsive interactions between the molecules exhibited a less pronounced increase in turbidity under forced oxidative stress. The stability of the formulations against oxidative stress was higher in the order from variant A>variant B>original XIAFLEX® formulation. The presence of detergents under forced oxidative stress had no influence on the turbidity of the samples. Without oxidative stress, all samples remained clear during thermal/agitation stress. Hydrophobic surface contact had no influence on the turbidity of the samples either with or without detergents during thermal/agitation stress.

Formulation Robustness Studies—Study 2

Twelve (12) formulation variants with different pH values and mannitol concentrations were investigated by CG-MALS and nanoDSC. Each variant was additionally exposed to thermal stress with agitation and to freeze/thaw stress testing. To force oxidative stress, each variant was supplemented with 0.1% H$_2$O$_2$. The objectives of this study were to:

Characterize the molecular interactions of the two protein species collagenase I and collagenase II in various formulation variants by means of CG-MALS and nano DSC; and Test the stability of XIAFLEX® and the additional formulation variants against freeze/thaw and thermal stress.

The following CCH formulations were prepared and tested:

TABLE 6

Formulations

| # | pH | Tris mM | Mannitol mM | Sucrose mM |
|---|---|---|---|---|
| 1 | 7.5 | 10 | 0 | 60 |
| 2 | 8.0 | 10 | 0 | 60 |
| 3 | 8.5 | 10 | 0 | 60 |
| 4 | 7.5 | 10 | 112.5 | 60 |
| 5 | 8.0 | 10 | 112.5 | 60 |
| 6 | 8.5 | 10 | 112.5 | 60 |
| 7 | 7.5 | 10 | 225 | 60 |
| 8 | 8.0 | 10 | 225 | 60 |
| 9 | 8.5 | 10 | 225 | 60 |
| 10 | 7.5 | 10 | 337.5 | 60 |
| 11 | 8.0 | 10 | 337.5 | 60 |
| 12 | 8.5 | 10 | 337.5 | 60 |

Collagenase I and collagenase II was dialyzed against the corresponding formulation buffer. After dialysis, the sample solutions were further diluted. Colloidal stability and thermodynamic stability of collagenase I, collagenase II, and the mixture was determined by CG-MALS and nanoDSC, respectively. The stability of the proteins in each formulation variant was additionally investigated in a stress test (freeze/thaw and thermal/shear stress) study. To force oxidative stress during the stability test, each formulation variant was examined in the presence and absence of 0.1% H$_2$O$_2$ (sub-variant without hydrogen peroxide are marked with a; sub-variant with hydrogen peroxide are marked with b).

Dialysis

The dialysis of collagenase I and collagenase II was accomplished in three independent dialysis steps to achieve a quantitative buffer exchange. 14 ml of the collagenase I intermediate sample and 14 ml of the collagenase II intermediate sample was transferred into two preconditioned (in dialysis buffer) Slide-A-Lyzer™ cassettes (Thermo Scientific, Rockford, USA). Filled Slide-A-Lyzer™ cassettes were incubated in 1000 ml of the target buffer for 2 hours before a first buffer change (1000 ml) was performed. After dialysis for two further hours the buffer was changed a second time (1000 ml) to finalize the dialysis overnight. The protein sample was removed from the Slide-A-Lyzer™ cassettes and processed further. Each dialysis step represents a 1/35 fold buffer exchange leading to a calculated buffer exchange factor of approx. 2×10$^5$ in total.

Nano Differential Scanning Calorimetry

Differential Scanning Calorimetry (DSC) is a technique used to assess the stability of a protein in its native form by measuring the heat change associated with the molecule's thermal denaturation when heated at a constant rate. A protein in solution is in equilibrium between its native (folded) and denatured (unfolded) conformations. Native proteins respond to heating by unfolding (thermal denaturation) at a characteristic temperature (T onset). The more intrinsically stable the biopolymer, the higher the onset temperature of the unfolding transition. DSC measures the enthalpy of unfolding that results from heat-induced denaturation and can elucidate factors that contribute to the folding and stability of native biomolecules. These include hydrophobic interactions, hydrogen bonding, conformational entropy, and the physical environment. The following experimental method was performed:

Mode: Scanning
Temperature parameters: Lower: 20° C.
  Upper: 100° C.
  Rate: 1° C./min heating and cooling
  Equilibration: 600 s
Pressure parameters: Manual, 3.0 atm
Data interval: 1 s A buffer scan was conducted prior to each sample run to generate a baseline. Sample preparation Dialyzed samples were diluted with the corresponding formulation buffer to 1 mg/ml. The corresponding dialysis buffer was used as buffer scan and buffer reference.

CG-MALS

Interactions between protein molecules in solution were characterized by analyzing changes in their light scattering behavior at different concentrations by calculating the second virial coefficient (A2). A2 is a measure of protein-protein interactions in solution. Negative $A_2$ values indicate attractive protein—protein interactions while positive values indicate repulsive protein interactions. A protein solution is "colloidally unstable" when the $A_2$ values are negative. A higher A2 value indicates greater repulsion, which is indicative of less protein interaction and less potential for protein aggregation and better stability. A2 values for various formulations were determined by CG-MALS and used as measures of non-specific protein-protein interactions The apparent weight average molecular weight ($Mw_{app}$) is determined for each step in the concentration gradient by analyzing the light scattering and concentration data. Significant interactions between macromolecules manifest as changes in $Mw_{app}$ vs. concentration. $A_2$ calculation was conducted via Zimm plot analysis by an extrapolation to 0 mg/ml concentration according to formula I below:

$$\frac{K^*c}{R(\theta, c)} = \frac{1}{M_w P(\theta)} + A_2 c \qquad \text{(Formula I)}$$

wherein:
R(θ,c): excess Rayleigh ratio of the solution as a function of scattering angle θ and concentration c. It is directly proportional to the intensity of the excess light scattered by the solute and the light scattered by the pure solvent.
Mw: Weight average molecular weight.
A2: 2nd virial coefficient
c: Concentration
K*: Optical constant $(4p^2(dn/dc)^2 n_0^2/N_a I_o^4)$
P(θ): describes the angular dependence of the scattered light, and can be related to the rms Radius.

Sample Preparation

Dialyzed samples were used undiluted for CG-MALS measurements. The corresponding dialysis buffer was used as diluent for the CG-MALS experiment. The samples and the buffer were passed over a 0.1 µm filter. Before loading the samples into the CG-MALS system the exact concentration of the samples was determined by UV-absorption measurement. The concentration was used to calculate the concentrations of each gradient step.

Sample Measurement

A Calypso II CG-MALS system was used to supply the MALS detector with the concentration gradient of the analyte. The samples were loaded on syringe pump 1 and syringe pump 2 of the system and the dialysis buffer on syringe pump 3. The CG-MALS measurement consisted of three steps. In the first step, a concentration gradient of sample 1 ranging from 10% to 100% was applied to determine the self-virial coefficient of sample 1 in the formulation. The second step consisted of a cross-over gradient, in which the concentration of sample 1 was reduced from 90% to 10% while the concentration of sample 2 was increased from 10% to 90%. This step was conducted to determine the cross-virial coefficient. In the third step, a concentration gradient of sample 2 ranging from 100% to 10% was applied to determine the self-virial coefficient of sample 2 in the formulation. At each gradient step 0.7 ml of sample was injected into the MALS detector. The resulted light scattering signal was recorded over a time period of 180 sec. Multi component Zimm plot analysis with fixed molecular weight was performed with Calypso software version 2.1.5.

UV Measurement

The concentration of collagenase I and collagenase II in solution was determined using an 8452A UV spectrometer (Agilent Technologies, Santa Clara, USA). Samples were measured at a concentration of about 3 mg/ml using plastic cuvettes with an optical path thickness of 0.2 cm. The concentration was calculated according to Lambert-Beer's law using an extinction coefficient of 1.52 ml/(mg*cm) for collagenase I and 1.48 ml/(mg*cm) for collagenase II, respectively.

Freeze/Thaw Testing

The freeze/thaw stability of the formulations was tested by running 3 freeze/thaw cycles in total. Dialyzed collagenase I and dialyzed collagenase II was mixed to exhibit a solution containing 0.5 mg/ml collagenase I and 0.5 mg/ml collagenase II.

2R glass vials were filled with 1.0 ml of each formulation. 3 vials were prepared for each variant. Liquid samples were frozen from 25° C. to −30° C. within 55 min at a controlled freezing rate and warmed up again to room temperature within 55 min at a controlled heating rate. For an adequate temperature control the samples were loaded into a pilot freeze dryer. After each freeze/thaw cycle, the turbidity of the samples was determined. For the turbidity measurement, 1 ml of each sample was filled in single-use turbidity cuvettes and analyzed. After analyzing, the liquid was returned to the glass vial and the experiment was continued.

Thermal Stress Test

Dialyzed collagenase I and dialyzed collagenase II was mixed to exhibit a solution containing 0.5 mg/ml collagenase I and 0.5 mg/ml collagenase II. Test samples of all formulations were stressed at 40° C. for 4 days under agitation (200 rpm) in 2R vials (1 ml fill volume). Turbidity of the stressed samples was analyzed afterwards.

Turbidity Measurement

The turbidity of the samples was determined as described above.

Results and Discussion

Table 7 shows the results of the CG-MALS and nanoDSC measurements of each formulation variant.

Colloidal stability—The pH value of the formulation showed a strong impact on the colloidal stability of collagenase I, collagenase II, and its mixture. Strongest repulsive interactions were observed at pH 8.5. At pH 7.5, the repulsive interactions were lower. At pH 7.5, collagenase I showed attractive interactions when mannitol was not present in the formulation and the repulsive interactions become stronger with higher concentrations of mannitol. At more basic pH values, the effect of mannitol became subordinated.

Thermodynamic stability—collagenase I showed a slight pH dependency of the onset temperature of unfolding. Higher T onset values were observed at pH 7.5 compared to pH 8.5. Mannitol showed slight and concentration dependent positive effect on the thermodynamic stability of collagenase I. The thermodynamic stability of collagenase II was independent from the investigated pH values. The presence of mannitol seemed to be beneficial for the thermodynamic stability of collagenase II.

TABLE 7

Results of the CG-MALS and nanoDSC analysis of the additional formulations

| | | Tris | Mannitol | Sucrose | A2 $10^{-4}$ mol*ml/g$^2$ | | | Nano DSC Tonset [° C.] | | Tm [° C.] | |
|---|---|---|---|---|---|---|---|---|---|---|---|
| # | pH | mM | mM | mM | AUX-1 | AUX-II | AUX-1 <> AUX-II | AUX-1 | AUX-II | AUX-1 | AUX-II |
| 1 | 7.5 | 10 | 0 | 60 | −0.32 | 0.51 | 0.19 | 47.1 | 51.2 | 51.3 | 54.8 |
| 2 | 8.0 | 10 | 0 | 60 | 0.03 | 0.91 | 0.65 | 46.9 | 51.7 | 51.8 | 55.1 |
| 3 | 8.5 | 10 | 0 | 60 | 1.93 | 1.52 | 1.68 | 46.4 | 51.0 | 51.7 | 55.0 |
| 4 | 7.5 | 10 | 112.5 | 60 | 0.24 | 0.32 | 0.51 | 49.1 | 51.3 | 52.6 | 55.6 |
| 5 | 8.0 | 10 | 112.5 | 60 | 0.99 | 1.25 | 0.96 | 47.2 | 51.6 | 51.9 | 55.4 |
| 6 | 8.5 | 10 | 112.5 | 60 | 2.33 | 1.95 | 1.75 | 47.0 | 51.9 | 52.0 | 55.6 |
| 7 | 7.5 | 10 | 225 | 60 | 0.76 | 1.69 | 0.94 | 49.5 | 53.0 | 53.2 | 56.2 |
| 8 | 8.0 | 10 | 225 | 60 | 1.93 | 1.77 | 1.24 | 48.8 | 53.2 | 53.2 | 56.2 |
| 9 | 8.5 | 10 | 225 | 60 | 2.22 | 1.97 | 1.43 | 48.8 | 53.0 | 53.0 | 56.0 |
| 10 | 7.5 | 10 | 337.5 | 60 | 1.58 | 1.79 | 0.91 | 49.9 | 52.6 | 53.4 | 56.4 |
| 11 | 8.0 | 10 | 337.5 | 60 | 2.04 | 1.62 | 0.82 | 48.8 | 53.9 | 53.1 | 56.3 |
| 12 | 8.5 | 10 | 337.5 | 60 | 1.69 | 2.03 | 1.33 | 49.0 | 53.9 | 53.3 | 56.3 |

Table 8 shows the turbidity values of the samples during the subsequent freeze thaw cycles.

TABLE 8

Turbidity values of the formulations with subsequent freeze/thaw cycles.

| | | Tris | Mannitol | Sucrose | H$_2$O$_2$ | | Turbidity [NTU] | | |
|---|---|---|---|---|---|---|---|---|---|
| # | pH | mM | mM | mM | % | T0 | 1x F/T | 2x F/T | 3x F/T |
| 1a | 7.5 | 10 | 0 | 60 | 0 | 2.1 | 3.0 | 2.8 | 2.6 |
| 2a | 8.0 | 10 | 0 | 60 | 0 | 2.2 | 2.2 | 3.5 | 2.2 |
| 3a | 8.5 | 10 | 0 | 60 | 0 | 2.8 | 1.8 | 3.8 | 2.1 |
| 4a | 7.5 | 10 | 112.5 | 60 | 0 | 2.4 | 2.5 | 3.4 | 2.1 |
| 5a | 8.0 | 10 | 112.5 | 60 | 0 | 3.0 | 2.6 | 3.0 | 2.3 |
| 6a | 8.5 | 10 | 112.5 | 60 | 0 | 2.6 | 1.9 | 3.5 | 2.5 |
| 7a | 7.5 | 10 | 225 | 60 | 0 | 1.8 | 2.8 | 3.6 | 2.5 |
| 8a | 8.0 | 10 | 225 | 60 | 0 | 2.5 | 3.2 | 2.2 | 2.4 |
| 9a | 8.5 | 10 | 225 | 60 | 0 | 2.7 | 3.0 | 3.0 | 2.5 |
| 10a | 7.5 | 10 | 337.5 | 60 | 0 | 2.8 | 2.8 | 3.0 | 2.3 |
| 11a | 8.0 | 10 | 337.5 | 60 | 0 | 2.6 | 3.0 | 3.4 | 3.3 |
| 12a | 8.5 | 10 | 337.5 | 60 | 0 | 2.5 | 2.9 | 3.0 | 2.2 |
| 1b | 7.5 | 10 | 0 | 60 | 0.1 | 1.9 | 2.2 | 3.3 | 2.6 |
| 2b | 8.0 | 10 | 0 | 60 | 0.1 | 2.6 | 2.6 | 2.1 | 3.1 |
| 3b | 8.5 | 10 | 0 | 60 | 0.1 | 2.6 | 1.8 | 2.1 | 1.8 |
| 4b | 7.5 | 10 | 112.5 | 60 | 0.1 | 2.8 | 2.8 | 3.6 | 2.9 |
| 5b | 8.0 | 10 | 112.5 | 60 | 0.1 | 1.9 | 2.8 | 3.3 | 2.3 |
| 6b | 8.5 | 10 | 112.5 | 60 | 0.1 | 2.2 | 2.2 | 2.1 | 2.6 |
| 7b | 7.5 | 10 | 225 | 60 | 0.1 | 2.3 | 2.6 | 2.1 | 2.9 |
| 8b | 8.0 | 10 | 225 | 60 | 0.1 | 2.6 | 2.2 | 3.7 | 2.4 |
| 9b | 8.5 | 10 | 225 | 60 | 0.1 | 1.9 | 2.9 | 2.5 | 3.6 |
| 10b | 7.5 | 10 | 337.5 | 60 | 0.1 | 2.2 | 2.7 | 1.9 | 3.1 |

TABLE 8-continued

Turbidity values of the formulations with subsequent freeze/thaw cycles.

| | | Tris | Mannitol | Sucrose | H$_2$O$_2$ | | Turbidity [NTU] | | |
|---|---|---|---|---|---|---|---|---|---|
| # | pH | mM | mM | mM | % | T0 | 1x F/T | 2x F/T | 3x F/T |
| 11b | 8.0 | 10 | 337.5 | 60 | 0.1 | 2.9 | 2.9 | 3.5 | 2.7 |
| 12b | 8.5 | 10 | 337.5 | 60 | 0.1 | 2.0 | 1.8 | 2.2 | 1.8 |

None of the variants showed an increase of turbidity after the freeze/thaw testing. The presence of hydrogen peroxide was well tolerated in each formulation under freeze/thaw stress.

Table 9 shows the turbidity values of each formulation before and after thermal stress.

TABLE 9

Turbidity values before and after thermal stress.

| | | Tris | Mannitol | Sucrose | H$_2$O$_2$ | | Turbidity [NTU] |
|---|---|---|---|---|---|---|---|
| # | pH | mM | mM | mM | % | T0 | 4 days/200 rpm/40° C. |
| 1a | 7.5 | 10 | 0 | 60 | 0 | 2.1 | 2.3 |
| 2a | 8.0 | 10 | 0 | 60 | 0 | 2.2 | 2.3 |
| 3a | 8.5 | 10 | 0 | 60 | 0 | 2.8 | 2.4 |
| 4a | 7.5 | 10 | 112.5 | 60 | 0 | 2.4 | 2.9 |
| 5a | 8.0 | 10 | 112.5 | 60 | 0 | 3.0 | 2.4 |
| 6a | 8.5 | 10 | 112.5 | 60 | 0 | 2.6 | 2.7 |
| 7a | 7.5 | 10 | 225 | 60 | 0 | 1.8 | 2.8 |
| 8a | 8.0 | 10 | 225 | 60 | 0 | 2.5 | 2.7 |
| 9a | 8.5 | 10 | 225 | 60 | 0 | 2.7 | 2.6 |
| 10a | 7.5 | 10 | 337.5 | 60 | 0 | 2.8 | 2.8 |
| 11a | 8.0 | 10 | 337.5 | 60 | 0 | 2.6 | 2.7 |
| 12a | 8.5 | 10 | 337.5 | 60 | 0 | 2.5 | 2.7 |
| 1b | 7.5 | 10 | 0 | 60 | 0.1 | 1.9 | 388.0 |
| 2b | 8.0 | 10 | 0 | 60 | 0.1 | 2.6 | 34.0 |
| 3b | 8.5 | 10 | 0 | 60 | 0.1 | 2.6 | 10.4 |
| 4b | 7.5 | 10 | 112.5 | 60 | 0.1 | 2.8 | 252.0 |
| 5b | 8.0 | 10 | 112.5 | 60 | 0.1 | 1.9 | 22.7 |
| 6b | 8.5 | 10 | 112.5 | 60 | 0.1 | 2.2 | 7.5 |
| 7b | 7.5 | 10 | 225 | 60 | 0.1 | 2.3 | 336.0 |
| 8b | 8.0 | 10 | 225 | 60 | 0.1 | 2.6 | 19.6 |

TABLE 9-continued

Turbidity values before and after thermal stress.

| # | pH | Tris mM | Mannitol mM | Sucrose mM | $H_2O_2$ % | T0 | Turbidity [NTU] 4 days/200 rpm/40° C. |
|---|---|---|---|---|---|---|---|
| 9b | 8.5 | 10 | 225 | 60 | 0.1 | 1.9 | 7.0 |
| 10b | 7.5 | 10 | 337.5 | 60 | 0.1 | 2.2 | 196.0 |
| 11b | 8.0 | 10 | 337.5 | 60 | 0.1 | 2.9 | 20.7 |
| 12b | 8.5 | 10 | 337.5 | 60 | 0.1 | 2.0 | 6.6 |

In the absence of oxygen radicals, the turbidity remained constant in all investigated formulation variants. In the presence of hydrogen peroxide, the turbidity of the samples increased strongly. This indicated that oxidative stress induced the formation of aggregates. More basic pH of 8.5 stabilized the proteins against aggregation induced by oxidative stress. Mannitol showed a further beneficial effect on the turbidity of the samples after thermal stress in the presence of hydrogen peroxide. Mannitol seemed to act as a radical scavenger improving the stability of the proteins against oxidative stress.

Formulation Robustness Studies—Study 3

The following study utilized sucrose and trehalose at concentrations of 60 mM and mannitol at 225 mM. Several concentrations of surfactant were evaluated and the concentration used for a given sample is noted in the data tables below. The effect of pH on various formulations pre-lyophilization was evaluated as a part of the formulation optimization.

The robustness of the proposed formulations as solutions was investigated by subjecting them to the following stresses:
  Three freeze-thaw cycles (−30° C. to 25° C.); and/or
  Shaking at 200 rpm at 40° C. for four days
The stressed samples were then tested for turbidity and the key product quality attributes were assessed using the following methods:
  Protein concentration by $UV_{A280}$
  Mass and Ratio of collagenase I and collagenase II by Reverse Phase—High Performance Liquid Chromatography (discussed herein)
  Soluble Rat Tail Collagen (SRC) Enzyme Activity Assay Method (collagenase I; discussed herein)
  Glycyl-L-prolyl-L-alanine (GPA) Enzyme Activity Assay Method (collagenase II; discussed herein)

Results

Turbidity: Data generated for freeze/thaw cycling are presented in Table 10.

TABLE 10

Effect of Freeze-Thaw Cycling on Product Turbidity

| Sample Description | | | | | Turbidity [NTU] Freeze-Thaw Cycle | | | |
|---|---|---|---|---|---|---|---|---|
| Stabilizer | Bulking Agent | Surfactant | pH | Container | $T_0$ | 1 | 2 | 3 |
| Trehalose | Mannitol | None | 8.5 | Glass type 1 | 3.2 | 3.2 | 2.8 | 2.5 |
| Trehalose | Mannitol | Polysorbate 20[a] | 8.5 | Glass type1 | 3.3 | 2.7 | 2.3 | 2.7 |
| Trehalose | Mannitol | None | 8.5 | Siliconized glass | 3.2 | 4.2 | 2.9 | 1.8 |
| Trehalose | Mannitol | Polysorbate 20[a] | 8.5 | Siliconized glass | 3.3 | 2.7 | 2.5 | 2.3 |
| Trehalose | Mannitol | None | 8.0 | Siliconized glass | 1.9 | 2.5 | 2.4 | 2.7 |
| Trehalose | Mannitol | Polysorbate 20[a] | 8.0 | Siliconized glass | 2.3 | 2.2 | 2.6 | 2.8 |
| Sucrose (control) | None | None | 8.0 | Siliconized glass | 2.3 | 1.9 | 1.9 | 3.0 |
| Sucrose | None | Polysorbate 20[a] | 8.0 | Siliconized glass | 2.7 | 2.4 | 2.5 | 2.9 |

[a]0.02%

These results demonstrated that multiple freeze-thaw cycles do not affect protein aggregation as indicated by the consistent turbidity values for any of the formulation/container combinations tested. The results indicated that the tested excipients were appropriate for further evaluation.

Data generated for shaking/exposure to high temperatures are presented in Table 11.

TABLE 11

Effect of Heat/Shaking on Product Turbidity

| Sample Description | | | | | Turbidity [NTU] | |
|---|---|---|---|---|---|---|
| Stabilizer | Bulking Agent | Surfactant | pH | Container | $T_0$ | After Mixing[a] |
| Trehalose | Mannitol | None | 8.5 | Glass type 1 | 3.2 | 3.1 |
| Trehalose | Mannitol | Polysorbate 20[b] | 8.5 | Glass type1 | 3.3 | 2.5 |
| Trehalose | Mannitol | None | 8.5 | Siliconized glass | 3.2 | 2.6 |
| Trehalose | Mannitol | Polysorbate 20[b] | 8.5 | Siliconized glass | 3.3 | 2.5 |
| Trehalose | Mannitol | None | 8.0 | Siliconized glass | 1.9 | 2.7 |
| Trehalose | Mannitol | Polysorbate 20[b] | 8.0 | Siliconized glass | 2.3 | 2.3 |
| Sucrose (Control) | None | None | 8.0 | Siliconized glass | 2.3 | 2.1 |
| Sucrose | None | Polysorbate 20[a] | 8.0 | Siliconized glass | 2.7 | 2.5 |

[a]After mixing at 40° C. and 200 rpm for 4 days
[b]0.02%

These results demonstrated that heat/shaking did not affect protein aggregation as indicated by the consistent turbidity values for any of the formulation/container combinations tested. The results indicate that the tested excipients were appropriate for further evaluation.

A second study was performed to evaluate the effect(s) of various concentrations of polysorbate 20 and higher pH (8.8) on product turbidity under stressed conditions. The results for this study are presented in Table 12.

TABLE 12

Effect of Surfactant Concentration on Product Turbidity Under Stress Conditions

| Sample Description | | | | Turbidity [NTU] | | | | |
|---|---|---|---|---|---|---|---|---|
| Stabilizer | Bulking Agent | Surfactant | pH | $T_0$ | Freeze Thaw Cycle 1 | 2 | 3 | Shaking[a] |
| Trehalose | Mannitol | Polysorbate 20[c] | 8.5 | 2.1 | 2.3 | 2.5 | 1.9 | 2.0 |
| Trehalose | Mannitol | None | 8.8 | 2.2 | 2.6 | 2.3 | 2.6 | 2.7 |
| None | Mannitol | Polysorbate 20[b] | 8.5 | 2.3 | 1.9 | 1.9 | 2.6 | 2.0 |
| Trehalose | None | Polysorbate 20[b] | 8.5 | 1.8 | 2.3 | 2.0 | 2.5 | 1.8 |
| Trehalose | None | None | 8.5 | 2.4 | 2.2 | 2.0 | 2.7 | 2.4 |

[a]After shaking at 40° C. and 200 rpm for 4 days
[b]0.02%
[c]0.1%

These data demonstrated that the surfactant levels studied (0.02% and 0.1%) and pH values of 8.5 and 8.8 have no negative impact on protein aggregation as indicated by consistent turbidity values upon freeze/thaw cycling or upon heat/shaking. The results indicated that thermodynamically stable formulations and use of polysorbate 20 as a surfactant in the concentration range studied can be considered. Further, the data also indicated that the use of trehalose or mannitol alone or in combination has no negative impact on the protein aggregation as measured by sample turbidity.

Key Product Quality Attribute Indicators—Data generated to assess the impact of freeze/thaw cycling for 3 cycles from −30° C. to 25° C. and of thermal stress/shaking of 40° C. and 200 rpm for 4 days are presented in Tables 13 and 14, respectively.

TABLE 13

Effect of Freeze/Thaw Cycles on Key Product Quality Attributes

| Sample Description | | | | | Results | | | | |
|---|---|---|---|---|---|---|---|---|---|
| | | | | | | Mass Ratio | | | |
| Stabilizer | Bulking Agent | Surfactant | pH | Vial | UV $A_{280}$ (mg/mL) | Coll. II (μg/mL) | Coll. I (μg/mL) | Ratio | SRC (Coll. I)[a] | GPA (Coll. II)[a] |
| Trehalose | Mannitol | None | 8.5 | Glass type1 | 1.0 | 483 | 488 | 1.0 | 1.04 | 1.05 |
| Trehalose | Mannitol | Polysorbate 20 | 8.5 | Glass type1 | 1.0 | 508 | 518 | 1.0 | 1.12 | 1.08 |
| Trehalose | Mannitol | None | 8.5 | Siliconized | 1.0 | 511 | 501 | 1.0 | 0.99 | 1.06 |
| Trehalose | Mannitol | Polysorbate 20 | 8.5 | Siliconized | 1.0 | 504 | 516 | 1.0 | 1.03 | 1.09 |
| Trehalose | Mannitol | None | 8.0 | Siliconized | 1.0 | 525 | 510 | 1.0 | 1.03 | 1.02 |
| Trehalose | Mannitol | Polysorbate 20 | 8.0 | Siliconized | 1.0 | 531 | 541 | 1.0 | 1.01 | 1.09 |
| Sucrose | None | None | 8.0 | Siliconized | 1.0 | 503 | 487 | 1.0 | 1.04 | 1.01 |
| Sucrose | None | Polysorbate 20 | 8.0 | Siliconized | 1.0 | 513 | 524 | 1.0 | 1.06 | 1.08 |
| Trehalose | Mannitol | Polysorbate 20[b] | 8.5 | Siliconized | 1.0 | 531 | 482 | 0.9 | 1.03 | 1.04 |
| Trehalose | Mannitol | None | 8.8 | Siliconized | 0.9 | 509 | 474 | 0.9 | 1.03 | 0.97 |
| None | Mannitol | Polysorbate 20[c] | 8.5 | Siliconized | 1.0 | 539 | 487 | 0.9 | 1.03 | 1.13 |
| Trehalose | None | Polysorbate 20[c] | 8.5 | Siliconized | 1.0 | 558 | 507 | 0.9 | 1.05 | 1.09 |
| Trehalose | None | None | 8.5 | Siliconized | 1.0 | 537 | 498 | 0.9 | 1.06 | 1.04 |

[a]Relative to Reference
[b]0.1%
[c]0.02%
Coll. I = collagenase I;
Coll. II = collagenase II

TABLE 14

Effect of 40° C. Temperature and Shaking at 200 rpm (4 Days) on Key Product Quality Attributes

| Sample Description | | | | | Result | | | | |
|---|---|---|---|---|---|---|---|---|---|
| | | | | | | Mass Ratio | | | |
| Stabilizer | Bulking Agent | Surfactant | pH | Vial | UV $A_{280}$ (mg/mL) | Coll. II (μg/mL) | Coll. I (μg/mL) | Ratio | SRC (Coll. I)[a] | GPA (Coll. II)[a] |
| Trehalose | Mannitol | None | 8.5 | Glass type1 | 1.0 | 474 | 474 | 1.0 | 0.96 | 0.95 |
| Trehalose | Mannitol | Polysorbate 20 | 8.5 | Glass type1 | 1.0 | 458 | 475 | 1.0 | 0.95 | 0.99 |
| Trehalose | Mannitol | None | 8.5 | Siliconized | 1.0 | 439 | 459 | 1.0 | 0.95 | 0.94 |
| Trehalose | Mannitol | Polysorbate 20 | 8.5 | Siliconized | 1.0 | 431 | 468 | 0.9 | 0.94 | 0.97 |
| Trehalose | Mannitol | None | 8.0 | Siliconized | 1.0 | 462 | 475 | 1.0 | 0.95 | 0.97 |
| Trehalose | Mannitol | Polysorbate 20 | 8.0 | Siliconized | 1.0 | 444 | 485 | 0.9 | 0.94 | 0.99 |
| Sucrose | None | None | 8.0 | Siliconized | 1.0 | 421 | 454 | 0.9 | 0.85 | 1.00 |
| Sucrose | None | Polysorbate 20 | 8.0 | Siliconized | 1.0 | 414 | 464 | 0.9 | 0.90 | 1.02 |
| Trehalose | Mannitol | Polysorbate 20[b] | 8.5 | Siliconized | 1.0 | 502 | 506 | 1.0 | 0.96 | 0.98 |

TABLE 14-continued

Effect of 40° C. Temperature and Shaking at 200 rpm (4 Days) on Key Product Quality Attributes

| Sample Description | | | | Result | | | | | |
|---|---|---|---|---|---|---|---|---|---|
| | | | | | Mass Ratio | | | | |
| Stabilizer | Bulking Agent | Surfactant | pH Vial | UV A$_{280}$ (mg/mL) | Coll. II (μg/mL) | Coll. I (μg/mL) | Ratio | SRC (Coll. I)$^a$ | GPA (Coll. II)$^a$ |
| Trehalose | Mannitol | None | 8.8 Siliconized | 0.9 | 472 | 501 | 1.1 | 1.00 | 1.03 |
| None | Mannitol | Polysorbate 20$^c$ | 8.5 Siliconized | 1.0 | 511 | 512 | 1.0 | 0.93 | 1.00 |
| Trehalose | None | Polysorbate 20$^c$ | 8.5 Siliconized | 1.0 | 524 | 521 | 1.0 | 0.96 | 0.99 |
| Trehalose | None | None | 8.5 Siliconized | 1.0 | 491 | 513 | 1.0 | 0.98 | 1.00 |

$^a$Relative to Reference
$^b$0.1%
$^c$0.02%
Coll. I = collagenase I;
Coll. II = collagenase II These data confirmed that the modification of the formulation with the three tested excipients at various pH levels has no adverse effect on the protein stability/concentration and enzymatic activity and that these components are all appropriate for further evaluation in the lyophilized formulations. pH values in the range tested also did not demonstrate adverse effect on product quality.

Formulation Robustness Studies—Study 4

Various formulations were also characterized by Composition-Gradient Multi-Angle Light Scattering (CG-MALS) to assess self- and hetero-protein interactions and Nano Differential Scanning Calorimetry (DSC) to assess protein unfolding as described. CG-MALS and nanoDSC were performed as described above.

A study was also conducted to determine if hydrogen peroxide as an oxidizing agent impacts the formulations being studied (solutions pre-lyophilization) based on turbidity values.

Results

CG-MALS—Results are presented in Table 15.

TABLE 15

Effect of Composition and pH on Protein Interactions by CG-MALS

| Variable Parameters | | | | CG-MALS A2 [10$^{-4}$ mol*mL/g$^2$] | | |
|---|---|---|---|---|---|---|
| pH | Sodium Chloride (mM) | Trehalose (mM) | Mannitol (mM) | Sucrose (mM) | Coll. I (self) | Coll. II (self) | Coll. I ↔ Coll. II (hetero) |
| 7.5 | None | 60 | 0 | 0 | 0.25 | 0.45 | 0.43 |
| 8.0 | None | 60 | 0 | 0 | 1.01 | 0.93 | 0.94 |
| 8.5 | None | 60 | 0 | 0 | 2.16 | 1.97 | 1.83 |
| 7.5 | 100 | 60 | 0 | 0 | 0.31 | 0.42 | 0.44 |
| 8.5 | 100 | 60 | 0 | 0 | 0.85 | 0.54 | 0.60 |
| 7.5 | None | 120 | 0 | 0 | 0.30 | 0.43 | 0.40 |
| 8.5 | None | 120 | 0 | 0 | 2.24 | 1.90 | 1.85 |
| 8.5 | 50 | 120 | 0 | 0 | 0.47 | 0.28 | 0.35 |
| 7.5 | 100 | 120 | 0 | 0 | 0.26 | 0.17 | 0.20 |
| 8.5 | 100 | 120 | 0 | 0 | 0.56 | 0.27 | 0.34 |
| 8.5 | None | 60 | 225 | 0 | 2.15 | 1.77 | 1.79 |
| 8.5 | None | 0 | 225 | 60 | 2.00 | 1.77 | 1.84 |

Coll. I = collagenase I;
Coll. II = collagenase II

For a given formulation composition, the highest repulsive interaction was observed at pH 8.5 within and across the proteins (collagenase I & collagenase II) as illustrated in FIG. 1 for the trehalose-containing formulations.

Trehalose, sucrose, and mannitol also do not adversely affect the repulsive forces and are therefore were appropriate potential components of the formulation.

Nano-DSC—The variables studied using Nano-DSC to assess protein unfolding (pH, type and concentration of excipient) are presented in Table 16.

TABLE 16

Effect of Composition and pH on Onset Temperature (T$_{onset}$) for Protein Unfolding and Protein Unfolding Temperature (T$_m$)

| Variable Parameters | | | | | Nano DSC | | | |
|---|---|---|---|---|---|---|---|---|
| | | | | | T$_{onset}$ [° C.] | | T$_m$ [° C.] | |
| pH | Sodium Chloride (mM) | Trehalose (mM) | Mannitol (mM) | Sucrose (mM) | Coll. I | Coll. II | Coll. I | Coll. II |
| 7.5 | None | 60 | None | None | 46.8 | 52.7 | 52.8 | 55.5 |
| 8.0 | None | 60 | None | None | 46.3 | 52.0 | 52.1 | 55.3 |
| 8.5 | None | 60 | None | None | 45.9 | 51.2 | 51.8 | 55.1 |
| 7.5 | 100 | 60 | None | None | 48.8 | 51.0 | 53.3 | 53.8 |
| 8.5 | 100 | 60 | None | None | 49.0 | 50.3 | 52.3 | 53.0 |
| 7.5 | None | 120 | None | None | 48.0 | 52.2 | 52.6 | 55.7 |
| 8.5 | None | 120 | None | None | 45.9 | 51.5 | 52.0 | 55.3 |
| 8.5 | 50 | 120 | None | None | 48.5 | 49.1 | 52.6 | 53.8 |
| 7.5 | 100 | 120 | None | None | 48.7 | 50.4 | 53.8 | 54.1 |
| 8.5 | 100 | 120 | None | None | 48.4 | 48.9 | 52.9 | 53.3 |
| 8.5 | None | 60 | 225 | None | 46.4 | 51.8 | 52.3 | 55.8 |
| 8.5 | None | 0 | 225 | 60 | 45.3 | 51.4 | 52.5 | 55.9 |

Coll. I = collagenase I;
Coll. II = collagenase II

The results demonstrated that the various formulation components studied had no impact on the onset temperature (T$_{onset}$) for protein unfolding and protein melting temperature (T$_m$). Furthermore, T$_{onset}$ data indicated that a temperature of 40° C. can be used successfully during the secondary drying step of the lyophilization process without affecting the protein stability.

Figure 2A:
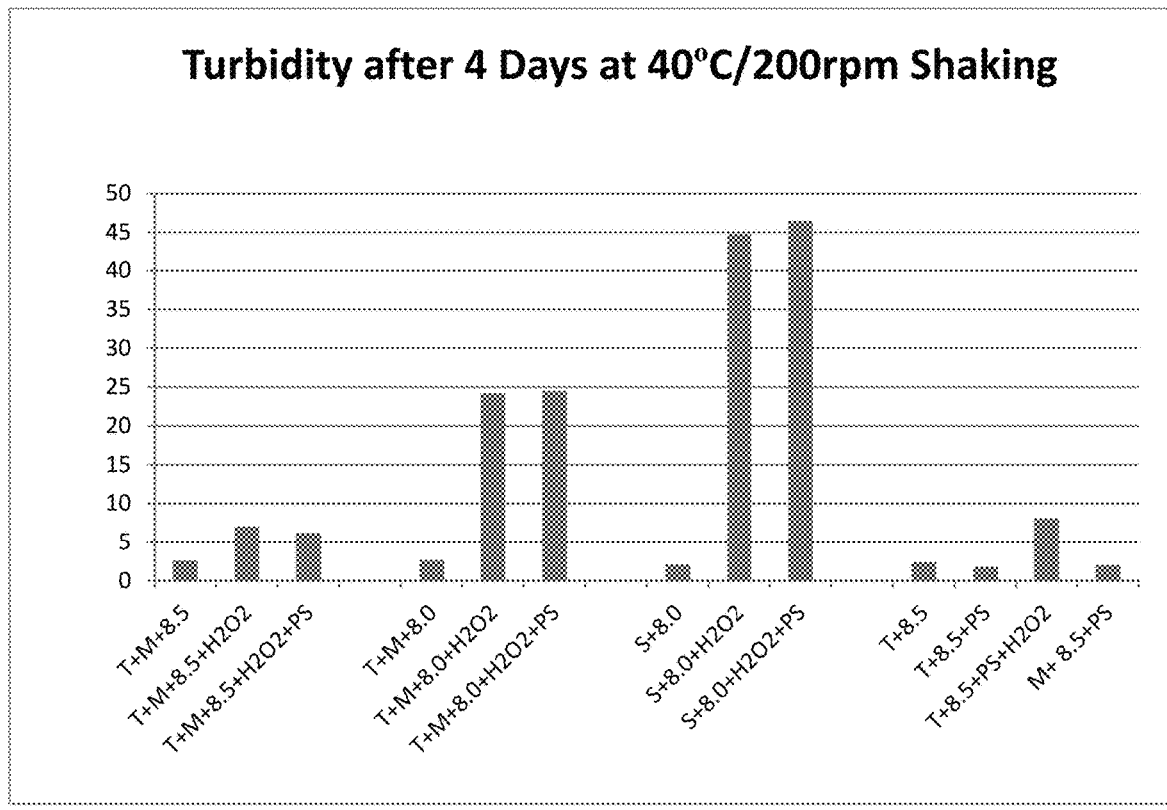
FIG. 2A and FIG. 2B illustrate an exemplary hydrogen peroxide challenges analyzing the effect of pH and excipients on turbidity. NTU—Nephelometric Turbidity Units; PS—Polysorbate; T—Trehalose, S—Sucrose, M—Mannitol; $H_2O_2$—Hydrogen peroxide; 7.5, 8.0, and 8.5 refers to formulation pH.
Figure 2B:
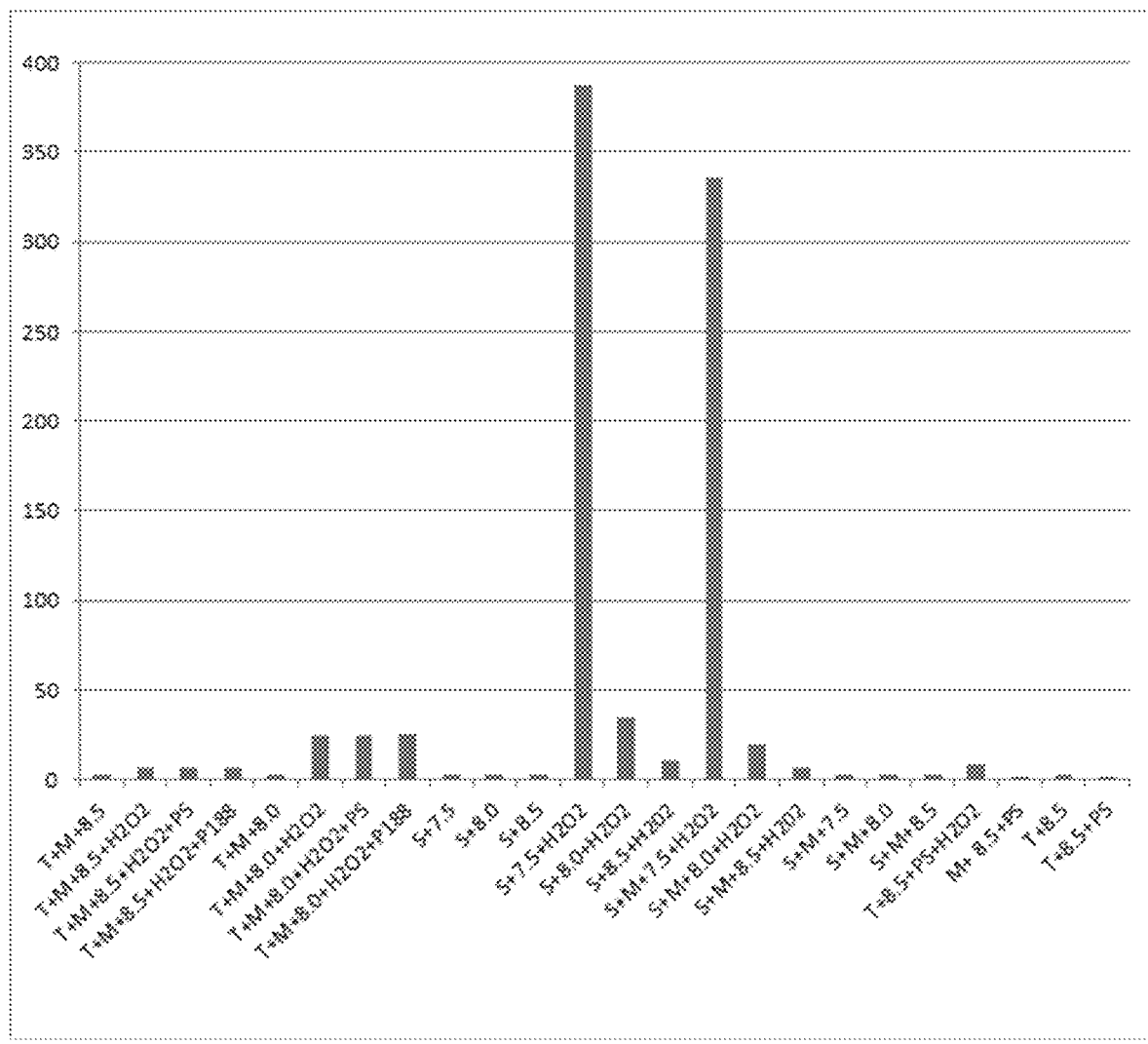

Hydrogen Peroxide Challenge—Hydrogen peroxide was used to challenge the formulations in a short term study (FIG. 2A and FIG. 2B). Trehalose-containing formulations (with or without mannitol) and sucrose-containing formulations (with and without mannitol) showed significantly lower turbidity at pH 8.5 compared to the same formulations at pH 8.0 and pH 7.5 after exposure to hydrogen peroxide. Lower turbidity values are indicative of a stable formulation with low protein aggregation. These results were in line with the high A2 values (high repulsive interaction) seen with formulation pH at 8.5 indicating the potential for improved stability. The results also indicated that, upon exposure to hydrogen peroxide, trehalose and mannitol-containing formulations with or without polysorbate (pH 8.0 or 8.5) showed significantly lower turbidity values compared to sucrose-containing formulations with no mannitol at pH 8.0. The presence of a surfactant had no positive or negative impact on turbidity.

Conclusion

Based on the results of the formulation optimization work, which identified optimal qualitative and quantitative excipient composition, the following formulations (pre-lyophilization) were taken forward for evaluation of the lyophilization cycle:
 CCH and sucrose with mannitol with or without polysorbate 20 at pH 8.5
 CCH and trehalose with mannitol with or without polysorbate 20 at pH 8.5

Note that the lowest concentration of polysorbate 20 studied (0.02%) was used for future analyses as the higher concentration offered no benefit.

The lyophilization cycle development for both formulation variants was conducted in 5 mL vials. Table 17 provides specifics on the formulations that were evaluated.

An intermediate lyophilization cycle ("Lyo cycle") was used to freeze dry the products (with a goal of about 36 hrs total cycle time). Provided below is information on the pilot freeze dryer used in these experiments:
 Manufacturer: Hof Sonderanlagenbau (Lohra, Germany)
 Shelf area: 0.5 m$^2$
 Ice condenser capacity: 10 kg
 Adjustable ice condenser temperature
 In-vial temperature recording
 Differential pressure measurement
 Connectable radiation cage Preparation of Packaging Materials Lyophilization stoppers were autoclaved at 121° C. for 15 min and dried for 8 hours at 105° C. Vials were rinsed with purified water and depyrogenized at 300° C. for 2 hours.

The formulation variants were prepared by dialysis. The dialysis of XIAFLEX® drug substance was accomplished in three independent dialysis steps to achieve a quantitative buffer exchange. 125 ml of the XIAFLEX® drug substance was dialyzed against variant a, b and c. XIAFLEX® drug substance was transferred into two preconditioned (in dialysis buffer) dialysis tubes. Filled dialysis tubes were incu-

TABLE 17

Lyophilization Trial Formulation Samples

| Experimental Formulation | CCH[a] | Stabilizer | Bulking Agent | Surfactant | Buffer |
|---|---|---|---|---|---|
| 1[b] | 0.9 mg/mL | 60 mM Sucrose | None | None | 10 mM Tris/HCl pH 8.0 |
| 2 | | 60 mM Sucrose | 225 mM Mannitol | None | 10 mM Tris/HCl pH 8.5 |
| 3 | | 60 mM Sucrose | 225 mM Mannitol | 0.02% Polysorbate 20 | 10 mM Tris/HCl pH 8.5 |
| 4 | | 60 mM Trehalose | 225 mM Mannitol | None | 10 mM Tris/HCl pH 8.5 |
| 5 | | 60 mM Trehalose | 225 mM Mannitol | 0.02% Polysorbate 20 | 10 mM Tris/HCl pH 8.5 |

[a]Collagenase clostridium histolyticum
[b]Control (approved XIAFLEX ® formulation)

Lyophilization Cycle Optimization—Study 1 Varying Mannitol Concentration

The objective of this work was to study the effect of varying ratios of mannitol with fixed concentration of sucrose in the absence of surfactant on the lyophilization process and cycle time. The following experimental variants were prepared along with placebo Lyo samples:

bated in 1 L of the target buffer for 2 hours before a first buffer change (1 L) was performed. After dialysis for two additional hours the buffer was changed a second time (2 L) to finalize the dialysis overnight. The protein sample was removed from the dialysis tube and the concentration was adjusted to 0.93 mg/ml (±10%) by dilution (concentration

TABLE 18

Compositions of the formulations

| Variant # | Packaging system | Formulation | Fill volume |
|---|---|---|---|
| Va | 5 ml glass vial | 0.93 mg/ml CCH; 60 mM Sucrose; 112.5 mM Mannitol; 10 mM Tris/HCl buffer pH 8.5 | 1 ml |
| Vb | 5 ml glass vial | 0.93 mg/ml CCH; 60 mM Sucrose; 225 mM Mannitol; 10 mM Tris/HCl buffer pH 8.5 | 1 ml |
| Vc | 5 ml glass vial | 0.93 mg/ml CCH; 60 mM Sucrose; 337.5 mM Mannitol; 10 mM Tris/HCl buffer pH 8.5 | 1 ml |
| Placebo | 5 ml glass vial | 60 mM Sucrose; 337.5 mM Mannitol; 10 mM Tris/HCl buffer pH 8.5 | 1 ml | was checked by UV 280 nm). As a control, XIAFLEX® drug substance was used without dialysis.

Filtration and Filling

The lyophilization solutions were passed over a 0.22 µm filter before filling. 1 ml of the corresponding lyophilization solution was filled into the vial.

Lyophilization

The filled vials with lyophilization-stoppers attached to the vials in "lyo-position" were loaded into the pilot freeze dryer. About 125 vials per formulation and 100 placebo vials of Vb were loaded. The lyophilization cycle was run with the following parameters:

Freezing temperature (shelf): −50° C.
Primary drying temperature (shelf): −10° C.
Secondary drying temperature (shelf): 40° C.
Pressure: 0.25 mbar
Cumulative time: approximately 41 hours To control product temperature during freeze drying, thermo couples were inserted into product vials. Pressure was controlled during lyophilization by using a Pirani-pressure sensor. Pressure regulation was managed via vacuum and dosing valve (nitrogen injection). Vials were closed at a pressure of 750 mbar under nitrogen atmosphere.

Karl-Fischer Titration

The content of one vial of the corresponding lyophilizate was weighed into a glass vial which was sealed with a crimp cap. The sample was transferred into the oven of the Karl-Fischer coulometer (756/774; Metrohm) which was heated to 100° C. The septum of the cap was penetrated by an injection needle, and the generated water vapor was directly transferred into the titration chamber of the Karl-Fischer coulometer via dry nitrogen. Measurement was repeated one time. Empty glass vials were used for blank correction.

Crystal Water Analysis

The oven sample processor 774 enables a unique temperature ramping method in Karl Fischer titration. The sample was heated up by a defined heating rate and the released water was directly transferred into the titration chamber of the Karl-Fischer coulometer. By recording the generated water and the water drift (µg water/min) depending on the oven temperature, specified events where water was released (e.g. the release of hydrate water) can be detected. 50 to 100 mg of the lyophilizates was weighted into an empty 6R type 1 glass vial and closed with an alu-crimp-cab. The sample was transferred into the oven of the sample processor. There the sample is heated up by a defined temperature ramp from 50° C. to 140° C. in 45 min (2° C./min). The ramp was concluded at 140° C. to exclude undesired Maillard-reactions.

Visual Appearance

Lyophilizates were removed from the vial by carefully breaking the glass vial and the lyophilization cake was cut vertically to screen its inner layer for collapse zones.

Scanning Electron Microscopy

Lyophilizates were analyzed by SEM to evaluate their microstructure. Lyophilizates were cut, and the vertical cross sections and top/bottom surfaces were analyzed via SEM at 50× and 150× magnification.

Reconstitution

Vials were reconstituted with 4 ml of a solution containing 0.03% calcium chloride and 0.66% sodium chloride. Time for complete dissolution of the lyophilizates was recorded.

Nano Differential Scanning Calorimetry

Nano DSC was performed as described above.

Sample Preparation

Lyophilization solutions and reconstituted lyophilizates were analyzed at a concentration of 0.93 mg CCH/ml. The corresponding buffer was used as buffer scan and buffer reference.

Results

The digital data acquisition proved that the freeze drying process was conducted as intended. As indicated by Pirani to conductivity pressure sensor difference, sublimation of the batch was finished after about 15 hours of total lyophilization time. The end of sublimation of each different sub-lot was indicated by the steep increase of the product temperature during primary drying.

The primary drying step was terminated after about 17 hours of total lyophilization time. After 18 hours of secondary drying one vial of each variant was removed from the freeze dryer and the residual moisture level was determined by Karl-Fischer titration while the secondary drying step was prolonged for the rest of the batch. The Karl-Fischer analysis revealed that the residual moisture level was already below the desired value. Thus, the rest of the batch was unloaded immediately after receiving these results. Total duration of secondary drying was 19 hours.

Visual appearance—All samples showed excellent macroscopic appearance without any signs of cake defects (data not shown).

Reconstitution behavior—Lyophilizates of all sub-lots showed quick and spontaneous dissolution within seconds (<30 sec.)

Residual moisture—Table 19 shows the residual moisture levels of the samples measured by Karl-Fischer titration.

TABLE 19

| Residual Moisture (n = 3) | | | |
| --- | --- | --- | --- |
| Sample | Residual Moisture [%] | | |
| Va | 0.16 | 0.16 | 0.17 |
| Vb | 0.24 | 0.22 | 0.27 |
| Vc | 0.16 | 0.13 | 0.16 |

Figure 3A:
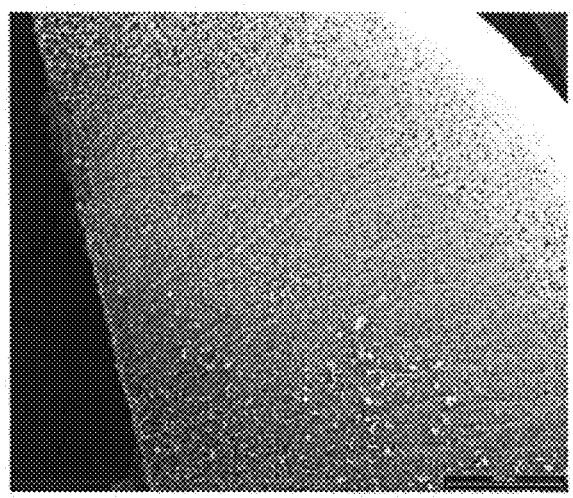
FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, and FIG. 3R illustrate scanning electron microscopy (SEM) images of cakes from various lyophilized formulations (Va: 0.93 mg/ml CCH; 60 mM Sucrose; 112.5 mM Mannitol; 10 mM Tris/HCl buffer pH 8.5; Vb: 0.93 mg/ml CCH; 60 mM Sucrose; 225 mM Mannitol; 10 mM Tris/HCl buffer pH 8.5; and Vc: 0.93 mg/ml CCH; 60 mM Sucrose; 337.5 mM Mannitol; 10 mM Tris/HCl buffer pH 8.5).
Figure 3B:
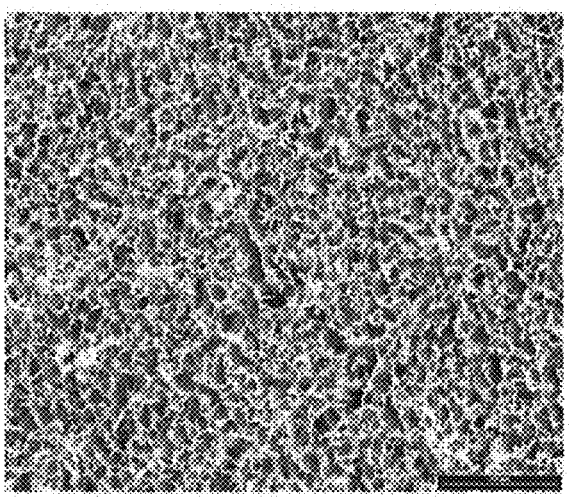
Figure 3C:
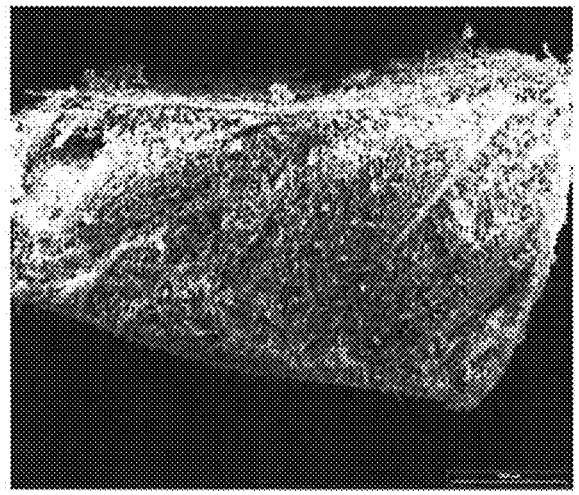
Figure 3D:
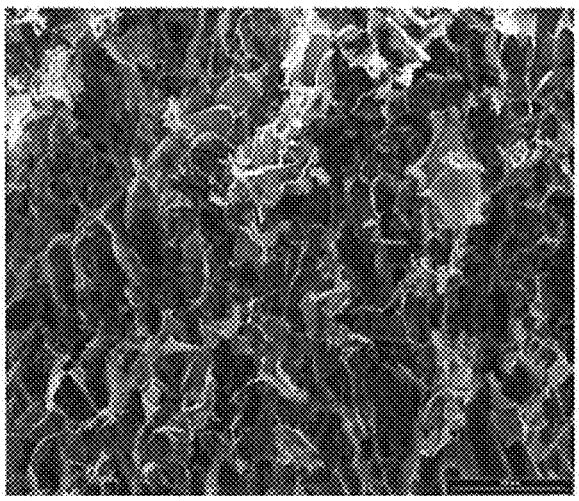
Figure 3E:
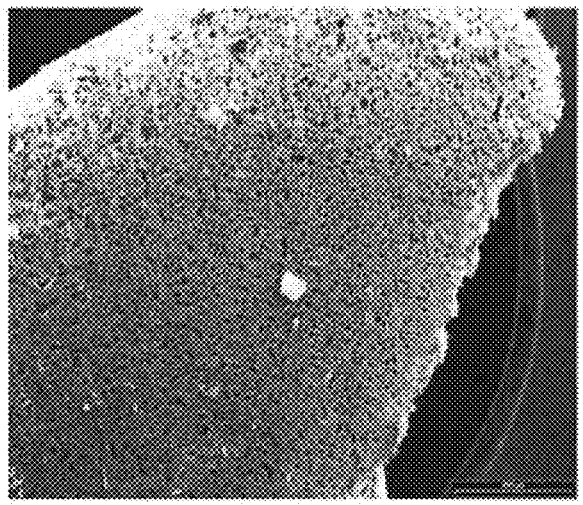
Figure 3F:
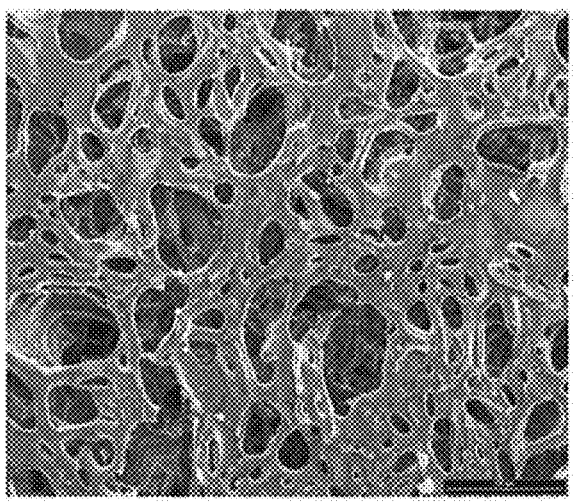
Figure 3G:
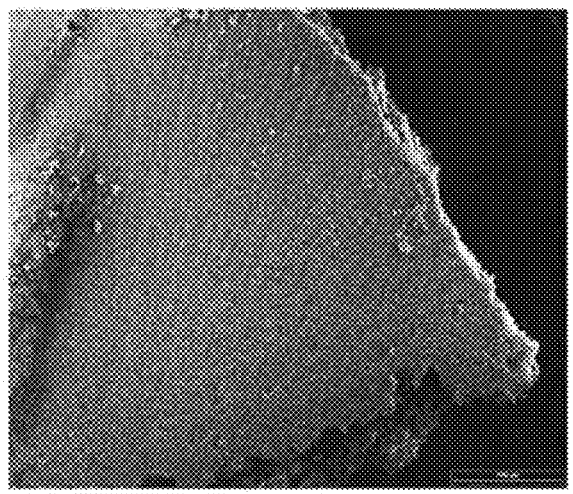
Figure 3H:
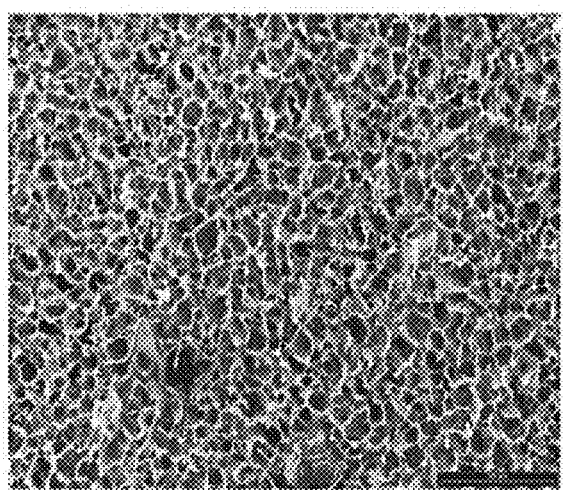
Figure 3I:
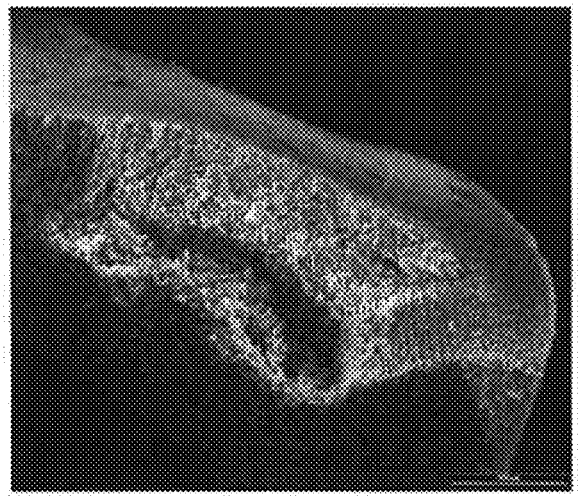
Figure 3J:
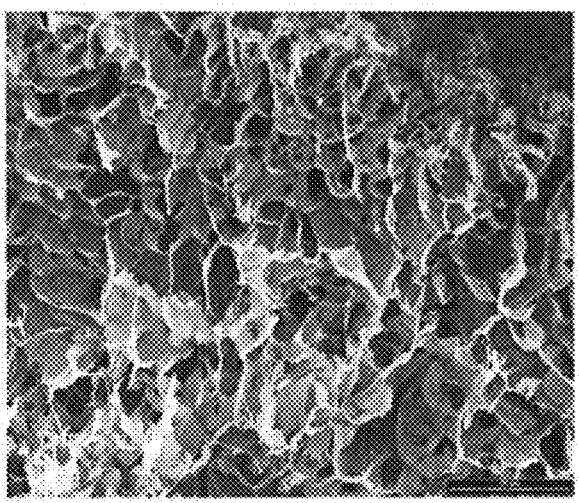
Figure 3K:
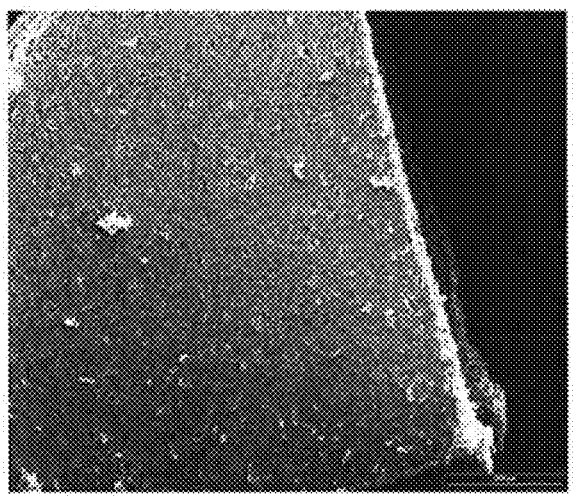
Figure 3L:
Figure 3M:
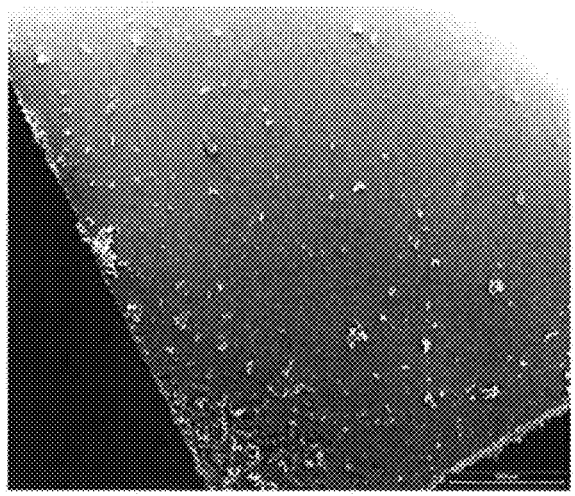
Figure 3N:
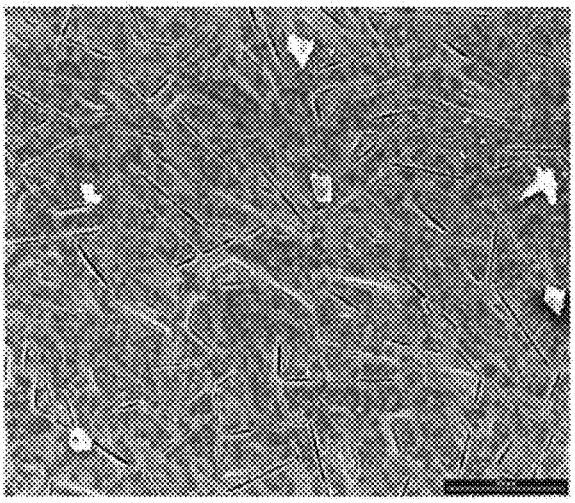
Figure 3O:
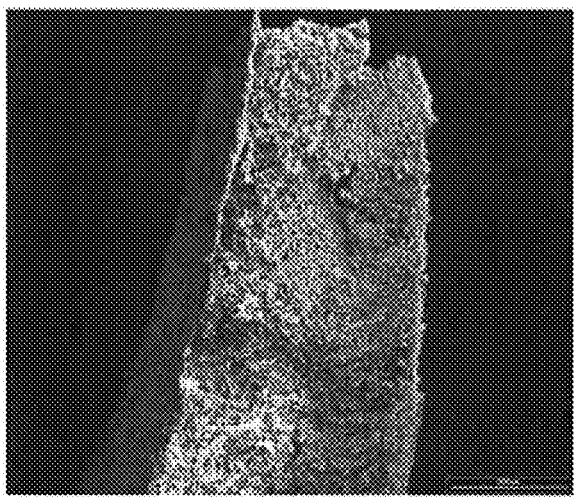
Figure 3P:
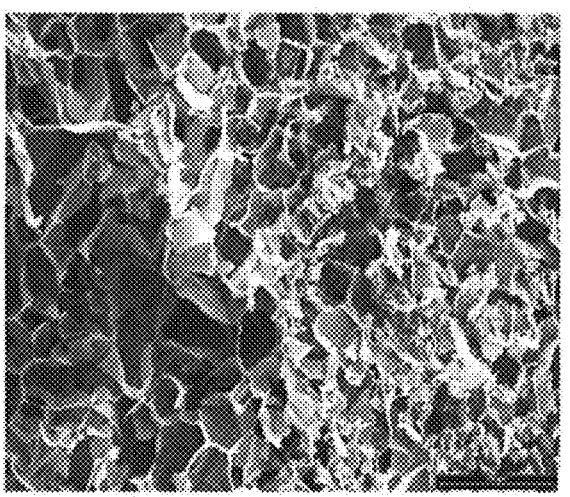
Figure 3Q:
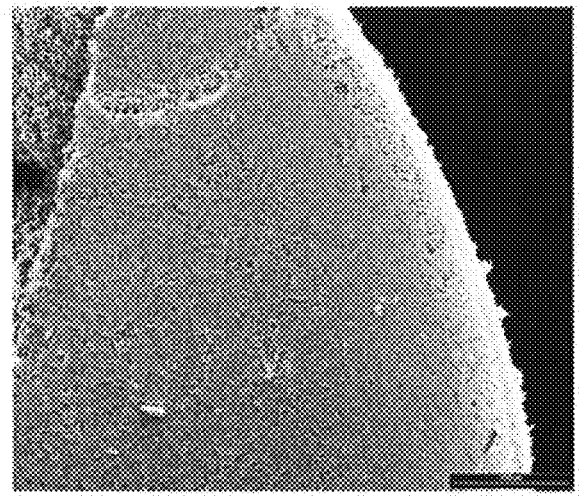
Figure 3R:
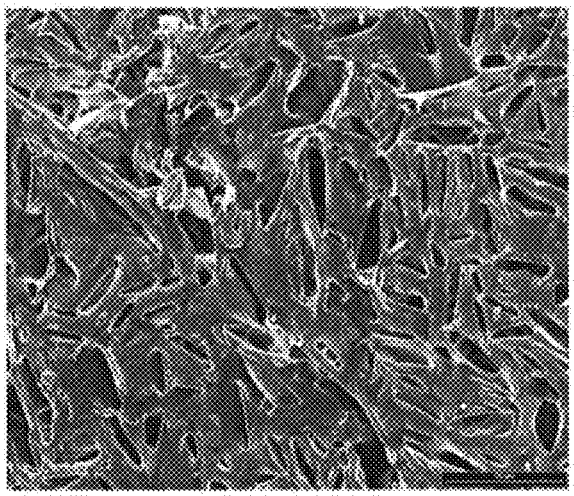

Scanning Electron Microscopy (SEM)—SEM analysis of the lyo cakes did not reveal any signs of collapse nor other cake defects (See FIG. 3A-FIG. 3R). The inner structure of all formulation variants was comparable. The top surface of variant Va (lowest amount of sucrose) had a more open-porous structure and showed less skin formation than variants Vb and Vc. The bottom surface of variant Vc looked more dense then the bottom surface of the other formulations.

Nano DSC—Table 20 summarizes the obtained results.

TABLE 20

| Results of the nano DSC Analysis Before and After Lyophilization | | | | | | |
| --- | --- | --- | --- | --- | --- | --- |
| | Before lyophilization | | | After lyophilization | | |
| Variant | Tm [° C.] | Tonset [° C.] | ΔH [kJ/mol] | Tm [° C.] | Tonset [° C.] | ΔH [kJ/mol] |
| Va | 54.9 | 47.9 | 1116 | 55.4 | 48.3 | 1140 |
| Vb | 55.4 | 48.2 | 1165 | 55.7 | 48.6 | 1183 |
| Vc | 56.1 | 49.2 | 1207 | 56.2 | 49.2 | 1124 |

To demonstrate the precision of the unfolding temperature and denaturation enthalpy, variant Vc (before lyophilization) was analyzed six times. The samples were derived from one sample preparation, which eliminated any concentration uncertainty. The difference between the results for T onset and Tm was below 1% whereas variation of the enthalpy was more than 7%, which is well in line with the specifications of the instrument (TA instruments states a uncertainty of 5% for the enthalpy of unfolding for lysozyme) (data not shown). It can be concluded that all formulations were equal before and after lyophilization within the error tolerances of the method in respect to unfolding temperature and transition enthalpy, indicating that the lyophilization process conditions used had no negative impact on the CCH. Increasing amounts of mannitol seem to result in an increased thermodynamic stability expressed by slightly higher values of Tm and T onset.

Conclusion

The observations and all of the data collected above indicate that the lyophilized formulations of CCH can be manufactured using a range of mannitol concentrations in presence of sucrose in Tris buffer. This work also identified more moderate lyophilization conditions leading to a cycle time of about 40 hrs.

Lyophilization Cycle Optimization—Study 2 Fixed Mannitol Concentration

The objective of this work was to update the lyophilization cycle to result in a shorter process time and more efficient and robust process.

Experimental Design

A laboratory scale lyophilization trial with the four experimental formulation variants along with the XIAFLEX® formulation as a control was completed using 5 cc vials. These variants are listed in Table 21 below.

TABLE 21

Lyophilization Trial Formulation Samples

Description (solution, pre-lyophilization)

| Experimental Formulation | CCH[a] | Stabilizer | Bulking Agent | Surfactant | Buffer |
|---|---|---|---|---|---|
| 1[b] | 0.9 mg/mL | 60 mM Sucrose | None | None | 10 mM Tris/HCl pH 8.0 |
| 2 | | 60 mM Sucrose | 225 mM Mannitol | None | 10 mM Tris/HCl pH 8.5 |
| 3 | | 60 mM Sucrose | 225 mM Mannitol | 0.02% Polysorbate 20 | 10 mM Tris/HCl pH 8.5 |
| 4 | | 60 mM Trehalose | 225 mM Mannitol | None | 10 mM Tris/HCl pH 8.5 |
| 5 | | 60 mM Trehalose | 225 mM Mannitol | 0.02% Polysorbate 20 | 10 mM Tris/HCl pH 8.5 |

[a]Collagenase clostridium histolyticum
[b]Control (approved XIAFLEX ® formulation)

To prepare experimental formulations #2-#5, formulation #1 was buffer exchanged using dialysis to introduce the new excipients (trehalose, mannitol, and polysorbate 20) into the formulation in Tris buffer, pH 8.5.

Initial lyophilization cycle development work was conducted using lyocycle conditions that are slightly more aggressive than the conditions used for the XIAFLEX® formulation in terms of drying temperatures, pressures, and times. Secondary drying was conducted at 40° C. to facilitate efficient drying of the product and achieve a target moisture of less than 0.5%. Comparative details of the XIAFLEX® process and the experimental lyophilization process are outlined in Table 22 below.

TABLE 22

Comparison of XIAFLEX ® (0.9 mg CCH/vial) and Experimental Lyocycle Process (0.92 mg CCH/vial)

| | XIAFLEX ® Process | Experimental Lyophilization Process |
|---|---|---|
| Freezing temperature | −50° C. | −50° C. |
| Primary drying temperature | −37° C. | −10° C. |
| Secondary drying temperature | 30° C. | 40° C. |
| Pressure | 40 microns | 188 millitorr |
| Cumulative time (approximate) | 70.5 hours | 57.5 hours |

Results and Conclusion

The lyophilized cakes for all formulations rapidly dissolved in the diluent with a reconstitution time of less than 10 seconds and had moisture contents (KF) of less than 0.4%.

At shortened experimental cycle time, the XIAFLEX® cake appeared shrunken compared to the experimental formulation variants, which all showed a well formed and robust cake. All of the experimental formulations were tested for various characteristics including protein concentration, collagenase I and collagenase II mass composition, and biologic activity. The test results for all of the formulations aligned with the XIAFLEX® formulation.

Experimental formulations #3 and #5 were selected for further testing. These formulations were used to conduct informal short term stability studies at 5° C. and at accelerated storage conditions of 25° C./60% RH. Samples were analyzed per approved test methods. All results generated for both formulations were in line with historical data for the XIAFLEX® formulation, indicating that the formulation changes being studied do not adversely affect product quality (data not shown). As noted previously, the currently approved limits may be revised based on a statistical analysis of data generated for the experimental formulations.

In summary, formulation optimization development work and data generated to date indicated that the two studied protein stabilizers (sucrose, trehalose), the addition of a bulking agent (mannitol), and a surfactant (polysorbate 20), do not adversely affect product quality and that these formulations would be suitable to pursue further.

Lyophilization Cycle Optimization—Study 3 Pressure Analysis

Study Objective

Pressure tests were performed to facilitate identification of the optimal lyophilization process conditions. This test set out to identify the maximum tolerable pressure and other reliable process parameters for freezing, primary drying, and secondary drying during lyophilization under process relevant conditions to realize a fast and robust lyophilization cycle.

Experimental Design

Three formulation variants in 5 cc vials were used as provided in Table 23.

TABLE 23

Lyophilization Trial Formulation Samples

| Experimental Formulation | CCH[a] | Stabilizer | Bulking Agent | Surfactant | Buffer |
|---|---|---|---|---|---|
| 1[b] | 0.9 mg/mL | 60 mM Sucrose | None | None | 10 mM Tris/HCl pH 8.0 |
| 3 | | 60 mM Sucrose | 225 mM Mannitol | 0.02% Polysorbate 20 | 10 mM Tris/HCl pH 8.5 |
| 5 | | 60 mM Trehalose | 225 mM Mannitol | 0.02% Polysorbate 20 | 10 mM Tris/HCl pH 8.5 |

Description (solution, pre-lyophilization)

[a]Collagenase clostridium histolyticum
[b]Control (approved XIAFLEX ® formulation)

To identify the pressure for the sublimation phase, two pressure tests were performed at different shelf temperatures and different pressure steps. Sample vials filled with the experimental formulations were loaded onto one freeze dryer shelf (middle position). After freezing, the chamber pressure was set to initial value of 128 µbar and shelf temperature was increased to an initial value (−10° C. in test 1/+10° C. in test 2). Lyophilization was allowed to run for a period of time to generate a small volume of lyophilizate above the ice interface. Chamber pressure was then increased step wise (e.g., 380 µbar, 1030 µbar etc.) and the sample vials were video monitored for cake collapse or other visual adverse effects. The shelf temperature was set to −10° C. to achieve a moderate energy input.

Figure 4A:
FIG. 4A, FIG. 4B, and FIG. 4C illustrate images of cakes from various lyophilized formulations under a pressure of 128 μbar (FIG. 4A), 380 μbar (FIG. 4B), and 1030 μbar (FIG. 4C).
Figure 4B:
Figure 4C:

Pictures of the vials at the end of each pressure step are presented in FIG. 4A-FIG. 4C. As shown in those figures, the Control (#1, XIAFLEX® in the vial shown on the far right) cake collapsed with increasing pressure. The maximum tolerable pressure for the XIAFLEX® formulation was therefore between 128 µbar and 380 µbar, equivalent to an ice interface temperature of between −40° C. and −30° C. Experimental Formulations #3 and #5 remained intact over the entire pressure range investigated.

A second pressure test was conducted, in which experimental formulations #3 and #5 were further investigated. The pressure range was expanded to 4 mbar. The temperature of the shelf during the test was set to +10° C. to provide sufficient energy input for enabling efficient sublimation at this pressure range.

Figure 5A:
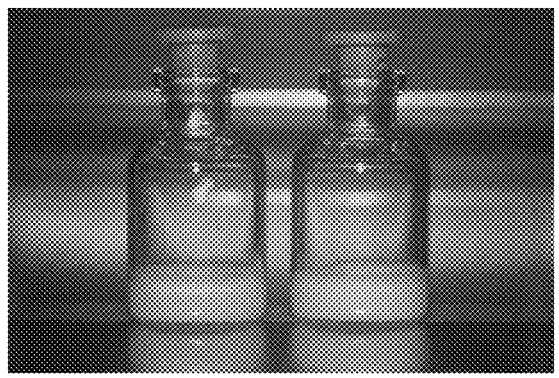
FIG. 5A and FIG. 5B illustrate images of cakes from various lyophilized formulations under a pressure of 128 μbar (FIG. 5A) and 4000 μbar (FIG. 5B).
Figure 5B:

The results are provided in FIG. 5A and FIG. 5B. No collapsed cakes or any other defects was observed over the entire pressure range investigated. Based on these findings, it was concluded that formulations containing mannitol can be freeze dried at a much higher chamber pressure, which will result in more efficient and robust lyophilization process with a shorter lyophilization cycle time.

This initial lyophilization cycle development work supported the use of mannitol to pursue a more efficient and robust lyophilization cycle.

Lyophilization Cycle Optimization—Study 4 Further Optimization

Based on the results of the pressure tests above, optimization of the lyophilization parameters was performed for experimental formulations #3 and #5 (data not shown).

As the pressure tests demonstrated that the mannitol-containing formulations can be freeze dried at chamber pressures up to 4 mbar with no risk of structural collapse during sublimation, the lyocycles for the optimization trials were run using a chamber pressure of 1 mbar to take advantage of high sublimation rates.

Two experimental lyocycle runs were performed to identify the basic parameters for a robust and efficient freeze drying cycle. Samples were analyzed post-lyophilization for visual appearance, residual moisture, physical stability, and by scanning electron microscopy (SEM).

Run #1: Utilized experimental formulation #3 only. Results from this run indicated that a higher temperature during secondary drying is required to reach a residual moisture level below 0.5%. Results for other physical attribute tests were acceptable (data not shown). A summary of the lyophilization parameters used are presented below:

Freezing temperature (shelf): −50° C.
Drying temperature (sublimation and secondary drying) (shelf): 35° C.
Pressure: 1 mbar
Cumulative time: approximately 21.5 hours Run #2: Utilized experimental formulation #3 only. This run identified adequate conditions for drying using 40° C. All results were acceptable (data not shown). A summary of the lyophilization parameters used are presented below:

Freezing temperature (shelf): −50° C.
Drying temperature (sublimation and secondary drying) (shelf): 40° C.
Pressure: 1 mbar
Cumulative time: approximately 21.5 hours Conclusions The lyocycle optimization studies identified basic parameters for an efficient freeze drying cycle. All tests for the physical attributes of the lyophilized cakes were acceptable.

Stability Studies—Long Term Stability Studies

Six process validation lots of the CCH formulation (1:1 mixture of collagenase I and collagenase II at a concentration of 1 mg/mL in 10 mM Tris, 60 mM sucrose, 225 mM mannitol, pH 8.5) were manufactured and placed on stability. One early formulation development lot, which utilized the same formulation but a lower fill quantity in a comparable container closure system, was manufactured and placed on stability.

The 6 process validation lots were monitored on long-term stability. Storage conditions included long-term stability at various storage condition (2–8° C.; 25° C./60% relative humidity (RH); and 40° C./75% RH) to support product shelf life as well as short-term stability studies at various storage conditions to support evaluation of potential temperature excursions during shipping or storage. Data for an early formulation development lot, which utilized the same formulation but a lower fill quantity (0.46 mg) in a comparable container closure system, was also included.

A summary of the studies along with available stability data is provided in Table 24.

TABLE 24

CCH Formulation Stability Study Summary

| Fill Quantity (mg CCH/vial) | Lot Number | Storage Condition | Length of Study (months) | Available Data (months) |
|---|---|---|---|---|
| 0.46 | 003H16 | 5° C. ± 3° C. | 36 | 36 |
|  |  | 25° C. ± 2° C./60% ± 5% RH | 36 | 36 |
|  |  | 40° C. ± 2° C./75% ± 5% RH | 6 | 6 |
| 0.92 | 307984 | 5° C. ± 3° C. | 36 | 24 |
|  |  | 25° C. ± 2° C./60% ± 5% RH | 36 | 24 |
|  |  | 40° C. ± 2° C./75% ± 5% RH | 6 | 6 |
|  | 307985 | 5° C. ± 3° C. | 36 | 24 |
|  |  | 25° C. ± 2° C./60% ± 5% RH | 36 | 24 |
|  |  | 40° C. ± 2° C./75% ± 5% RH | 6 | 6 |
|  | 313877 | 5° C. ± 3° C. | 36 | 18 |
|  |  | 25° C. ± 2° C./60% ± 5% RH | 36 | 18 |
|  |  | 40° C. ± 2° C./75% ± 5% RH | 6 | 6 |
| 1.84 | 320971 | 5° C. ± 3° C. | 36 | 12 |
|  |  | 25° C. ± 2° C./60% ± 5% RH | 36 | 12 |
|  |  | 40° C. ± 2° C./75% ± 5% RH | 6 | 6 |
|  | 320972 | 5° C. ± 3° C. | 36 | 12 |
|  |  | 25° C. ± 2° C./60% ± 5% RH | 36 | 12 |
|  |  | 40° C. ± 2° C./75% ± 5% RH | 6 | 6 |
|  | 320973 | 5° C. ± 3° C. | 36 | 12 |
|  |  | 25° C. ± 2° C./60% ± 5% RH | 36 | 12 |
|  |  | 40° C. ± 2° C./75% ± 5% RH | 6 | 6 |

Stability batches were tested for appearance (pre- and post-reconstitution), reconstitution time, osmolality, pH, concentration by $UV_{A280}$, quantitative sodium dodecyl sulfate polyacrylamide gel electrophoresis (SDS-PAGE), reverse-phase high performance liquid chromatography (RP-HPLC) [purity], mass and ratio by composition by RP-HPLC, size-exclusion high-performance liquid chromatography (SEC-HPLC), soluble rat tail collagen (SRC) assay for collagenase I potency, glycyl-L-prolyl-L-alanine (GPA) assay for collagenase II potency, moisture, particulates, endotoxin, and container closure integrity helium leak.

Results and Analysis

Assessments of the stability results along with a trending analysis for each test at various storage condition (2–8° C.; 25° C./60% relative humidity (RH); and 40° C./75% RH), as applicable, are outlined below:

Appearance (Pre- and Post-Reconstitution)—The results for appearance (pre- and post-reconstitution) at the storage conditions tested showed no significant changes or unexpected trends (data not shown).

Reconstitution Time—The results for reconstitution time at the storage conditions tested showed no significant changes or unexpected trends (data not shown).

Osmolality—The results for osmolality at the storage conditions tested showed no significant changes or unexpected trends (data not shown).

pH—The results for pH at the storage conditions tested showed no significant changes or unexpected trends (data not shown).

Concentration by $UV_{A280}$—The results for concentration by $UV_{A280}$ at the storage conditions tested showed no significant changes or unexpected trends (data not shown).

Quantitative SDS-PAGE—The results for quantitative SDS-PAGE at the storage conditions tested showed no significant changes or unexpected trends (data not shown).

RP-HPLC (Purity)—The results for RP-HPLC (purity) at the storage conditions tested showed no significant changes or unexpected trends (data not shown).

Mass and Ratio Composition by RP-HPLC—The results for mass and ratio by composition RP-HPLC at the storage conditions tested showed no significant changes or unexpected trends (data not shown).

SEC-HPLC—The results for SEC-HPLC at the storage conditions tested showed no significant changes or unexpected trends (data not shown).

SRC Assay for collagenase I Potency—The results for SRC assay for collagenase I potency at the storage conditions tested showed no significant changes or unexpected trends (data not shown).

GPA Assay for collagenase II Potency—The results for GPA assay for collagenase II potency at the storage conditions tested showed no significant changes or unexpected trends (data not shown).

Figure 6:
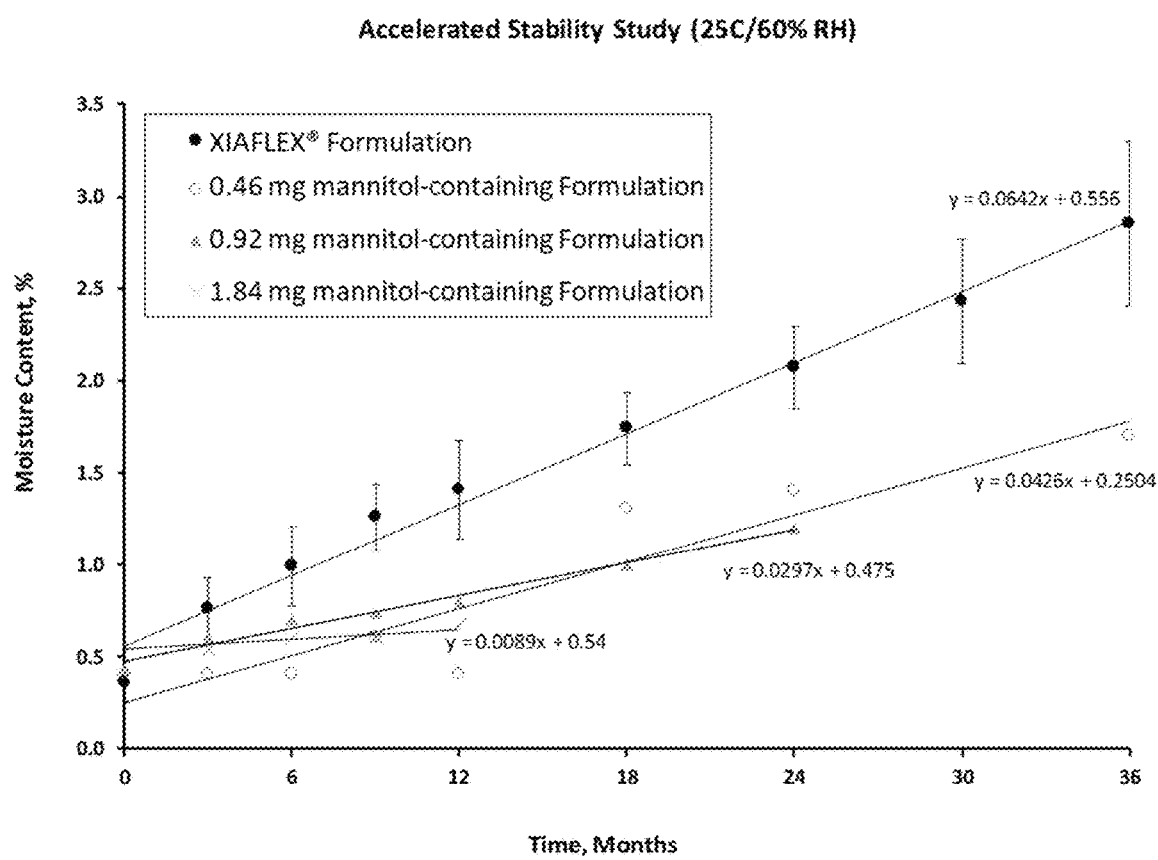
FIG. 6 illustrates the moisture content over time in various lyophilized formulations.

Moisture—As shown in FIG. 6, at 25° C./60% relative humidity, the mannitol-containing formulations showed less moisture than the XIAFLEX® formulation, indicating the improved stability of the mannitol-containing formulations.

Particulates—The results for particulates at the storage conditions tested showed no significant changes or unexpected trends (data not shown).

Container Closure Integrity/Helium Leak—The results for container closure integrity/helium leak showed no significant changes or unexpected trends (data not shown).

Photostability Study

A study was conducted to determine photostability of the CCH formulation following exposure to 1.2 million lux hours of cool, white light followed by 200 watt hours/square meter (W/m²) of UV energy. Samples were exposed to 8.00 kilolux of cool, white light for 150 hours, followed by exposure to 10.00 W/m² UV light for 20 hours. All results following this exposure were comparable to an unexposed control (data not shown).

Reconstitution Stability Study

To demonstrate compatibility of the lyophilized CCH formulation with the sterile diluent used for reconstitution and to generate stability data for the reconstituted product under potential in-use conditions, several reconstitution stability studies were executed. The lyophilized CCH formulation was reconstituted with sterile diluent and subjected to analysis at specified time points following storage at specified temperatures. Table 25 summarizes the reconstitution stability studies performed.

TABLE 25

Summary of Reconstitution Stability Studies

| Fill Quantity (mg CCH/vial) | Description of Study |
|---|---|
| 0.92 | Temperature Cycling: Following reconstitution with diluent and storage at 25° C./60% RH for 24 hours, then at 2° C.-8° C. for 96 hours and then at 25° C./60% RH for an additional 24 hours (testing at T0 and end of study) 25° C./60% RH for 24 hours: Following reconstitution with diluent and storage at 25° C./60% RH for 24 hours (testing at T0 and end of study) 2° C.-8° C. for 120 hours: Following reconstitution with diluent and storage at 2° C.-8° C. for 120 hours (testing at T0, 24 hours, 96 hours, and 120 hours) |
| 1.84 | Temperature Cycling: Following reconstitution with diluent and storage at 25° C./60% RH for 24 hours, then at 2° C.-8° C. for 96 hours and then at 25° C./60% RH for an additional 24 hours (testing at T0 and end of study) 25° C./60% RH for 24 hours: Following reconstitution with diluent and storage at 25° C./60% RH for 24 hours (testing at T0 and end of study) 2° C.-8° C. for 120 hours: Following reconstitution with diluent and storage at 2° C.-8° C. for 120 hours (testing at T0, 24 hours, 96 hours and 120 hours) |

All results at time zero and subsequent stability time points were comparable and no trends in the data noted (data not shown). These studies utilized microplate versions of the SRC and GPA test methods for determination of potency as these are higher throughput and quicker turnaround than the cuvette-based test methods; for each, the overall analytical approach of the microplate test method is the same as the cuvette test method. These results demonstrated compatibility of the lyophilized CCH formulation and the sterile diluent as well as demonstrated the stability of the reconstituted CCH formulation under potential conditions of use.

Conclusion

Available stability data for the 6 process validation lots of CCH formulation demonstrated stability of the material through at least the 18-month pull point at both 5° C. and 25° C./60% RH storage conditions, as well as through the 6-month pull point at the 40° C./75% RH storage condition. Additionally, available data for a formulation development lot of the CCH formulation in a smaller vial demonstrated stability through the 24-month pull point at both the and 25° C./60% RH storage conditions as well as through the 6-month pull point at the 40° C./75% RH storage condition.

The CCH formulation demonstrated acceptable photostability as all results generated following exposure were comparable to a control (unexposed) sample.

Following reconstitution with sterile diluent, CCH formulation showed acceptable stability for up to 24 hours when stored at 25° C./60% RH and for up 120 hours when stored at 5° C. Reconstituted CCH formulation also demonstrated acceptable stability when stored at 25° C./60% RH for 24 hours, then at 2° C. to 8° C. for 96 hours and then at 25° C./60% RH for an additional 24 hours.

Future annual stability studies will be conducted and include storage at 5° C.±3° C. and 25° C.±2° C./60%±5% RH conditions. Material at both storage conditions will be evaluated through the proposed 36-month shelf life.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1

A formulation comprising:
a collagenase;
about 30 mM to about 240 mM of a disaccharide;
about 50 mM to about 800 mM of mannitol; and
about 6 mM to about 10 mM of a Tris-HCl.

Embodiment 2

The formulation of embodiment 1, wherein the collagenase comprises a collagenase I.

Embodiment 3

The formulation of embodiment 2, wherein the collagenase I comprises the amino acid sequence of SEQ ID NO: 1.

Embodiment 4

The formulation of embodiment 1, wherein the collagenase comprises a collagenase II.

Embodiment 5

The formulation of embodiment 4, wherein the collagenase II comprises the amino acid sequence of SEQ ID NO: 2.

Embodiment 6

The formulation of embodiment 1, wherein the collagenase comprises a mixture of collagenase I and collagenase II.

Embodiment 7

The formulation of embodiment 6, wherein the collagenase I comprises the amino acid sequence of SEQ ID NO: 1 and the collagenase II comprises the amino acid sequence of SEQ ID NO: 2.

Embodiment 8

The formulation of embodiment 6 or 7, wherein the collagenase is collagenase *Clostridium histolyticum* (CCH).

Embodiment 9

The formulation of any one of the previous embodiments, wherein the disaccharide comprises sucrose or trehalose.

Embodiment 10

The formulation of any one of the previous embodiments, wherein the pH of the formulation is about 7.8 to about 8.8.

Embodiment 11

The formulation of any one of the previous embodiments, wherein the formulation comprises:
 CCH;
 about 60 mM sucrose;
 about 225 mM mannitol; and
 about 10 mM Tris-HCl,
 wherein the formulation has a pH of about 8.5.

Embodiment 12

The formulation of any one of the previous embodiments, further comprising a surfactant comprising polysorbate 20, polysorbate 80, or poloxamer 188.

Embodiment 13

The formulation of embodiment 12, comprising from about 0.01% to about 2% of the surfactant.

Embodiment 14

The formulation of embodiment 13, comprising about 0.02% of the surfactant.

Embodiment 15

The formulation of any one of the previous embodiments, wherein the formulation is liquid.

Embodiment 16

A lyophilized formulation comprising:
 a collagenase;
 a disaccharide;
 mannitol; and
 Tris-HCl.

Embodiment 17

The lyophilized formulation of embodiment 16, wherein the collagenase comprises a collagenase I.

Embodiment 18

The lyophilized formulation of embodiment 17, wherein the collagenase I comprises the amino acid sequence of SEQ ID NO: 1.

Embodiment 19

The lyophilized formulation of embodiment 16, wherein the collagenase comprises a collagenase II.

Embodiment 20

The lyophilized formulation of embodiment 19, wherein the collagenase II comprises the amino acid sequence of SEQ ID NO: 2.

Embodiment 21

The lyophilized formulation of embodiment 16, wherein the collagenase comprises a mixture of collagenase I and collagenase II.

Embodiment 22

The lyophilized formulation of embodiment 21, wherein the collagenase I comprises the amino acid sequence of SEQ ID NO: 1 and the collagenase II comprises the amino acid sequence of SEQ ID NO: 2.

Embodiment 23

The lyophilized formulation of embodiment 21 or 22, wherein the collagenase is collagenase *Clostridium histolyticum* (CCH).

Embodiment 24

The lyophilized formulation of any one of embodiments 16-23, wherein the disaccharide comprises sucrose or trehalose.

Embodiment 25

The lyophilized formulation of any one of embodiments 16-24, wherein, prior to lyophilization, the formulation comprises:
 CCH;
 60 mM sucrose;
 225 mM mannitol; and
 10 mM Tris-HCl, and
 having a pH of about 8.5.

Embodiment 26

The lyophilized formulation of any one of embodiments 16-25, wherein the lyophilized formulation is stable at pressures above 380 µbar.

Embodiment 27

The lyophilized formulation of embodiment 26, wherein the lyophilized formulation is stable at a pressure of about 4000 μbar.

Embodiment 28

The lyophilized formulation of any one of embodiments 16-27, wherein the lyophilized formulation is stable at:
(e) 2–8° C. for at least 36 months;
(f) 25° C./60% relative humidity for at least 36 months;
(g) 40° C./75% relative humidity for at least 6 months; or
(h) any combination of (a) to (c).

Embodiment 29

The lyophilized formulation of any one of embodiments 16-28, wherein the lyophilized formulation is formed by a method comprising:
freezing the formulation at a temperature between about −25° C. and −55° C. to form a frozen formulation; and
drying the frozen formulation at a temperature between about 25° C. and about 50° C. to form the lyophilized formulation.

Embodiment 30

The lyophilized formulation of embodiment 29, wherein the lyophilized formulation is formed by a method comprising:
freezing the formulation at a single temperature between about −25° C. and −55° C. to form a frozen formulation; and
drying the frozen formulation at a single temperature between about 25° C. and about 50° C. to form the lyophilized formulation.

Embodiment 31

The lyophilized formulation of any one of embodiments 16-30, wherein the lyophilized formulation is formed by a lyophilization method that is performed for less than 72 hours.

Embodiment 32

The lyophilized formulation of any one of embodiments 16-31, wherein the lyophilized formulation is formed by a lyophilization method that is performed at a pressure of between about 380 μbar to about 4000 μbar.

Embodiment 33

The lyophilized formulation of any one of embodiments 16-32, in a unit-dose vial, multi-dose vial, cartridge, or syringe.

Embodiment 34

A reconstituted formulation comprising:
a collagenase;
a disaccharide;
mannitol;
Tris-HCl;
calcium chloride; and
sodium chloride.

Embodiment 35

The reconstituted formulation of embodiment 34, wherein the collagenase is collagenase *Clostridium histolyticum* (CCH).

Embodiment 36

The reconstituted formulation of embodiment 34 or 35, wherein the disaccharide comprises sucrose or trehalose.

Embodiment 37

The reconstituted formulation of any one of embodiments 34-36, wherein the reconstituted formulation is isotonic to human blood.

Embodiment 38

A kit comprising:
a container comprising the lyophilized formulation of any one of embodiments 16-32; and
a container comprising a sterile diluent comprising calcium chloride and sodium chloride.

---

What is claimed:

1. A formulation comprising:
a collagenase;
about 30 mM to about 240 mM of a disaccharide;
about 50 mM to about 800 mM of mannitol; and
about 6 mM to about 10 mM of Tris-HCl.

2. The formulation of claim 1, wherein the collagenase is produced by recombinant techniques.

3. The formulation of claim 1, wherein the disaccharide is sucrose or trehalose.

4. The formulation of claim 1, wherein the pH of the formulation is about 7.8 to about 8.8.

5. The formulation of claim 1, wherein the formulation comprises:
a collagenase;
about 60 mM of sucrose;
about 225 mM of mannitol; and
about 10 mM of Tris-HCl,
wherein the formulation has a pH of about 8.5.

6. The formulation of claim 1, further comprising a surfactant selected from polysorbate 20, polysorbate 80, and poloxamer 188.

7. The formulation of claim 6, comprising from about 0.01% to about 2% of the surfactant.

8. The formulation of claim 7, comprising about 0.02% of the surfactant.

9. The formulation of claim 1, wherein the formulation is liquid.

* * * * *